United States Patent
Brookhart et al.

(10) Patent No.: US 7,060,768 B2
(45) Date of Patent: Jun. 13, 2006

(54) POLYMERIZATION OF OLEFINIC COMPOUNDS

(75) Inventors: Maurice S. Brookhart, Chapel Hill, NC (US); Keith Kunitsky, West Grove, PA (US); Weijun Liu, Carrboro, NC (US); Jon M. Malinoski, Chapel Hill, NC (US); Lin Wang, Hockessin, DE (US); Ying Wang, West Chester, PA (US); Lynda Kaye Johnson, Wilmington, DE (US); Kristina A. Kreutzer, Wilmington, DE (US); Steven Dale Ittel, Wilmington, DE (US)

(73) Assignees: E.I. duPont de Nemours and Company, Wilmington, DE (US); University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/761,030

(22) Filed: Jan. 20, 2004

(65) Prior Publication Data

US 2004/0158012 A1 Aug. 12, 2004

Related U.S. Application Data

(62) Division of application No. 10/057,090, filed on Jan. 25, 2002, now Pat. No. 6,710,007.

(60) Provisional application No. 60/294,794, filed on May 31, 2001, provisional application No. 60/264,537, filed on Jan. 28, 2001.

(51) Int. Cl.
  *C08F 4/44* (2006.01)
  *C08F 4/72* (2006.01)

(52) U.S. Cl. ............ 526/161; 526/171; 526/172; 502/155; 502/167; 556/35; 556/137; 556/138

(58) Field of Classification Search ........... 526/161, 526/171, 172; 556/35, 137, 138; 502/155, 502/167
See application file for complete search history.

(56) References Cited

U.S. PATENT DOCUMENTS

| | | | |
|---|---|---|---|
| 4,906,754 A * | 3/1990 | Klabunde | 546/2 |
| 5,714,556 A | 2/1998 | Johnson et al. | |
| 5,880,241 A | 3/1999 | Brookhart et al. | |
| 6,103,658 A * | 8/2000 | Mackenzie et al. | 502/167 |

* cited by examiner

*Primary Examiner*—Robert D. Harlan

(57) ABSTRACT

Certain complexes containing ligands having a phosphino group, amino group or an imino group, and a second functional group such as amide, ester or ketone, when complexed to transition metals, catalyze the (co)polymerization of olefinic compounds such as ethylene, α-olefins and/or acrylates. A newly recognized class of ligands for making copolymer containing polar monomers using late transition metal complexes is described.

4 Claims, No Drawings

POLYMERIZATION OF OLEFINIC COMPOUNDS

FIELD OF THE INVENTION

The polymerization of olefins is catalyzed by transition metal complexes of selected imines, amines or phosphines containing another group such as ester or amide, and in some instances other olefinic compounds such as unsaturated esters may be copolymerized with olefins. Useful transition metals include Ni, Fe, Ti and Zr. Certain types of late transition metal complexes are especially useful in making polymers containing polar comonomers.

TECHNICAL BACKGROUND

The polymerization of olefins such as ethylene and propylene is a very important commercial activity, and such polymers in various forms are made in enormous quantities for very many uses. Various methods are known for polymerizing olefins, such as free radical polymerization of ethylene, and coordination polymerization using catalysts such as Ziegler-Natta-type and metallocene-type catalysts. Nevertheless, given the importance of polyolefins new catalysts are constantly being sought for such polymerizations, to lower the cost of production and/or make new, and hopefully improved, polymer structures. More recently so-called single site catalysts using late transition metal complexes have been developed, and they have proved in many instances to give different polymers than the earlier known early transition metal catalysts. See, for example, U.S. Pat. No. 5,714,556, U.S. Pat. No. 5,880,241 and U.S. Pat. No. 6,103,658 (all of which are incorporated by reference herein for all purposes as if fully set forth).

Another type of useful polyolefin is one that contains polar comonomers, such as acrylates. These copolymers are made especially well by a new type of complex in which a certain type of ligand is used.

SUMMARY OF THE INVENTION

This invention concerns new transition metal complexes, and processes for the polymerization of olefins using such new transition metal complexes.

A first aspect of the present invention concerns a Group 3 through 11 (IUPAC) transition metal or a lanthanide metal complex of a ligand of the formula (I)

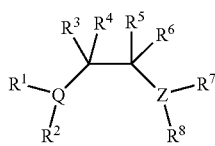

(I)

wherein:
Z is nitrogen or oxygen; and
Q is nitrogen or phosphorous;

provided that:
when Q is phosphorous and Z is nitrogen: $R^1$ and $R^2$ are each independently hydrocarbyl, silyl, or substituted hydrocarbyl having an $E_s$ of about –0.90 or less; $R^3$, $R^4$, $R^5$, and $R^6$ are each independently hydrogen, hydrocarbyl, a functional group, or substituted hydrocarbyl; $R^7$ is hydrogen, hydrocarbyl, substituted hydrocarbyl, or silyl; and $R^8$ is hydrocarbyl, substituted hydrocarbyl or silyl; provided that any two of $R^3$, $R^4$, $R^5$, $R^6$, $R^7$ and $R^8$ vicinal or geminal to one another together may form a ring;

when Q is phosphorous and Z is oxygen:
$R^1$ and $R^2$ are each independently hydrocarbyl, silyl, or substituted hydrocarbyl having an $E_s$ of about –0.90 or less; $R^3$ and $R^4$ are each independently hydrogen, hydrocarbyl, a functional group, or substituted hydrocarbyl; $R^5$ and $R^7$ taken together form a double bond; $R^8$ is not present; and $R^6$ is —$OR^9$, —$NR^{10}R^{11}$, hydrocarbyl or substituted hydrocarbyl, wherein $R^9$ is hydrocarbyl or substituted hydrocarbyl, and $R^{10}$ and $R^{11}$ are each independently hydrogen, hydrocarbyl or substituted hydrocarbyl; and provided that any two of $R^3$, $R^4$, and $R^6$ vicinal or geminal to one another may form a ring; or $R^1$ and $R^2$ are each independently hydrocarbyl, silyl, or substituted hydrocarbyl having an $E_s$ of about –0.90 or less; $R^3$, $R^4$, $R^5$ and $R^6$ are each independently hydrogen, hydrocarbyl, a functional group, or substituted hydrocarbyl; $R^7$ is hydrocarbyl, silyl, or substituted hydrocarbyl; and $R^8$ is not present; and provided that any two of $R^3$, $R^4$, $R^5$, $R^6$, and $R^7$ vicinal or geminal to one another may form a ring;

when Q is nitrogen: $R^1$ is hydrocarbyl, silyl, or substituted hydrocarbyl having an $E_s$ of about –0.90 or less; $R^2$ and $R^3$ are each independently hydrogen, hydrocarbyl, a functional group, or substituted hydrocarbyl, or taken together form a double bond; $R^4$ is hydrogen, hydrocarbyl, a functional group, or substituted hydrocarbyl; Z is oxygen; $R^6$ and $R^7$ taken together form a double bond; $R^8$ is not present; $R^5$ is —$OR^{12}$, —$R^{13}$ or —$NR^{14}R^{15}$, wherein $R^{12}$ and $R^{13}$ are each independently hydrocarbyl or substituted hydrocarbyl, and $R^{14}$ and $R^{15}$ are each hydrogen, hydrocarbyl or substituted hydrocarbyl; provided that when $R^2$ and $R^3$ taken together form an aromatic ring, $R^1$ and $R^4$ are not present; and further provided that any two of $R^2$, $R^3$, $R^4$ and $R^5$ vicinyl or germinal to one another together may form a ring.

A second aspect of the present invention concerns a "first" process for the polymerization of olefins, comprising the step of contacting, under polymerizing conditions, one or more polymerizable olefins with an active polymerization catalyst comprising the aforementioned transition metal complex.

A third aspect of this invention is a "second" process for the manufacture of a polar copolymer by contacting, under polymerizing conditions, a hydrocarbon olefin, a polar olefin, and a polymerization catalyst comprising a nickel complex of a bidentate ligand which is an active ligand. This third aspect also includes an improved process for the manufacture of a polar copolymer by contacting, under polymerizing conditions, a hydrocarbon olefin, a polar olefin, and a polymerization catalyst comprising a nickel complex, wherein the improvement comprises that the polymerization catalyst comprises a nickel metal complex of a bidentate ligand which is an active ligand.

These and other features and advantages of the present invention will be more readily understood by those of ordinary skill in the art from a reading of the following detailed description. It is to be appreciated that certain features of the invention which are, for clarity, described below in the context of separate embodiments, may also be provided in combination in a single embodiment. Conversely, various features of the invention which are, for brevity, described in the context of a single embodiment, may also be provided separately or in any subcombination.

DETAILED DESCRIPTION OF THE PREFERRED EMBODIMENTS

Herein, certain terms are used. Some of them are:

A "hydrocarbyl group" is a univalent group containing only carbon and hydrogen. If not otherwise stated, it is preferred that hydrocarbyl groups (and alkyl groups) herein contain 1 to about 30 carbon atoms.

By "substituted hydrocarbyl" herein is meant a hydrocarbyl group that contains one or more substituent groups which are inert under the process conditions to which the compound containing these groups is subjected (e.g., an inert functional group, see below). The substituent groups also do not substantially detrimentally interfere with the polymerization process or operation of the polymerization catalyst system. If not otherwise stated, it is preferred that substituted hydrocarbyl groups herein contain 1 to about 30 carbon atoms. Included in the meaning of "substituted" are chains or rings containing one or more heteroatoms, such as nitrogen, oxygen and/or sulfur, and the free valence of the substituted hydrocarbyl may be to the heteroatom. In a substituted hydrocarbyl, all of the hydrogens may be substituted, as in trifluoromethyl.

By "(inert) functional group" herein is meant a group other than hydrocarbyl or substituted hydrocarbyl that is inert under the process conditions to which the compound containing the group is subjected. The functional groups also do not substantially interfere with any process described herein that the compound in which they are present may take part in. Examples of functional groups include halo (fluoro, chloro, bromo and iodo), and ether such as —OR$^{22}$ wherein R$^{22}$ is hydrocarbyl or substituted hydrocarbyl. In cases in which the functional group may be near a transition metal atom the functional group should not coordinate to the metal atom more strongly than the groups in those compounds are shown as coordinating to the metal atom, that is they should not displace the desired coordinating group.

By "silyl" herein is meant a monovalent group whose free valence is to a silicon atom. The other three valencies of the silicon atom are bound to other groups such as alkyl, halo, alkoxy, etc. Silyl groups are also included in functional groups.

By a "cocatalyst" or a "catalyst activator" is meant one or more compounds that react with a transition metal compound to form an activated catalyst species. One such catalyst activator is an "alkyl aluminum compound" which, herein, is meant a compound in which at least one alkyl group is bound to an aluminum atom. Other groups such as, for example, alkoxide, hydride and halogen may also be bound to aluminum atoms in the compound.

By "neutral Lewis base" is meant a compound, which is not an ion, which can act as a Lewis base. Examples of such compounds include ethers, amines, sulfides, olefins, and organic nitrites.

By "neutral Lewis acid" is meant a compound, which is not an ion, which can act as a Lewis acid. Examples of such compounds include boranes, alkylaluminum compounds, aluminum halides, and antimony [V] halides.

By "cationic Lewis acid" is meant a cation which can act as a Lewis acid. Examples of such cations are sodium and silver cations.

By an "empty coordination site" is meant a potential coordination site on a transition metal atom that does not have a ligand bound to it. Thus if an olefin molecule (such as ethylene) is in the proximity of the empty coordination site, the olefin molecule may coordinate to the metal atom.

By a "ligand into which an olefin molecule may insert between the ligand and a metal atom", or a "ligand that may add to an olefin", is meant a ligand coordinated to a metal atom which forms a bond (L-M) into which an olefin molecule (or a coordinated olefin molecule) may insert to start or continue a polymerization. For instance, with ethylene this may take the form of the reaction (wherein L is a ligand):

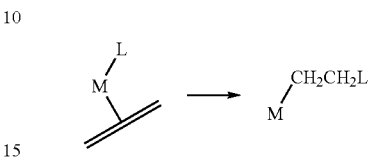

By a "ligand which may be displaced by an olefin" is meant a ligand coordinated to a transition metal which, when exposed to the olefin (such as ethylene), is displaced as the ligand by the olefin.

By a "monoanionic ligand" is meant a ligand with one negative charge.

By a "neutral ligand" is meant a ligand that is not charged.

"Alkyl group" and "substituted alkyl group" have their usual meaning (see above for substituted under substituted hydrocarbyl). Unless otherwise stated, alkyl groups and substituted alkyl groups preferably have 1 to about 30 carbon atoms.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

By "R$^x$ and R$^y$ taken together may form a double bond" is meant a structure originally written as —CRR$^x$—CRRY$^y$— is, when R$^x$ and R$^y$ do in fact form a double bond, —CR═CR—. In this example each R is simply another group on a carbon atom to satisfy carbon's normal valence requirement of 4.

By a "π-allyl group" is meant a monoanionic ligand comprised of 1 sp$^3$ and two sp$^2$ carbon atoms bound to a metal center in a delocalized η$^3$ fashion indicated by

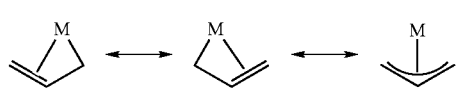

The three carbon atoms may be substituted with other hydrocarbyl groups or functional groups.

By "E$_s$" is meant a parameter to quantify steric effects of various groupings, see R. W. Taft, Jr., *J. Am. Chem. Soc.*, vol. 74, p. 3120–3128 (1952), and M. S. Newman, *Steric Effects in Organic Chemistry*, John Wiley & Sons, New York, 1956, p. 598–603, which are both hereby included by reference.

For the purposes herein, the $E_s$ values are those described for o-substituted benzoates in these publications. If the value of $E_s$ for a particular group is not known, it can be determined by methods described in these references.

By "under polymerization conditions" is meant the conditions for a polymerization that are usually used for the particular polymerization catalyst system being used. These conditions include things such as pressure, temperature, catalyst and cocatalyst (if present) concentrations, the type of process such as batch, semibatch, continuous, gas phase, solution or liquid slurry etc., except as modified by conditions specified or suggested herein. Conditions normally done or used with the particular polymerization catalyst system, such as the use of hydrogen for polymer molecular weight control, are also considered "under polymerization conditions". Other polymerization conditions such as presence of hydrogen for molecular weight control, other polymerization catalysts, etc., are applicable with this polymerization process and may be found in the references cited herein.

By a "hydrocarbon olefin" is meant an olefin containing only carbon and hydrogen.

By a "polar (co)monomer" or "polar olefin" is meant an olefin which contains elements other than carbon and hydrogen. When copolymerized into a polymer the polymer is termed a "polar copolymer". Useful polar comonomers are found in U.S. Pat. No. 5,866,663, WO 9905189, WO 9909078 and WO 9837110, and S. D. Ittel, et al., Chem. Rev., vol. 100, p.1169–1203 (2000), all of which are incorporated by reference herein for all purposes as if fully set forth. Also included as a polar comonomer is CO (carbon monoxide).

For ease in describing the invention, the term "transition metal" as used herein generally refers to Groups 3 through 11 of the periodic table (IUPAC) and the lanthanides, especially those in the 4th, 5th, 6th, and 10th periods. Suitable transition metals include Ni, Pd, Cu, Pt, Fe, Co, Ti, Zr, V, Hf, Cr, Ru, Rh and Re, with Ni, Fe, Ti, Zr, Cu and Pd being more preferred and Ni, Fe, Ti and Zr being especially preferred. Preferred oxiation states for some of the transition metals are Ni[II], Ti[IV], Zr[IV], and Pd[II].

The first polymerizations herein are carried out by a transition metal complex of (I).

Transition metal complexes in which (I) appears may, for example, have the formula (IV)

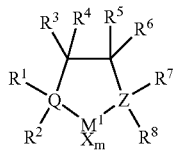

(IV)

wherein $R^1$ through $R^8$, Q and Z are as defined above; $M^1$ is a transition metal; each X is independently a monoanion; and m is an integer equal to an oxidation state of $M^1$.

Transition metal complexes in which (I) appears may, for example, also have the formula (IX)

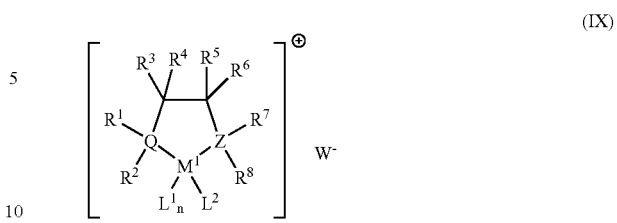

(IX)

wherein $R^1$ through $R^8$, Q and Z are as defined above; $M^1$ is a transition metal; $L^1$ is a monoanionic ligand which may add to an olefin; n is equal to the oxidation state of $M^1$ minus one; $L^2$ is a ligand which may be displaced by an olefin or is an empty coordination site; or $L^1$ and $L^2$ taken together are a bidentate monoanionic ligand into which an olefin molecule may insert between the ligand and a metal atom; and W is a relatively noncoordinating anion.

In (I) and in all complexes and compounds containing (I), it is preferred that:

when Q is nitrogen:
 $R^1$ is (VII) (see below) or a 2,5-disubstituted pyrrole, more preferably (VII); and/or
 $R^4$ is alkyl, especially alkyl containing 1 to 6 carbon atoms, more preferably methyl; and/or
 $R^5$ is —$OR^{12}$, —$R^{13}$ or —$NR^{14}R^{15}$; and/or
 $R^{12}$ is alkyl, especially alkyl containing 1 to 6 carbon atoms; and/or
 $R^{13}$ is alkyl, especially alkyl containing 1 to 6 carbon atoms; and/or
 $R^{14}$ is alkyl containing 1 to 6 carbon atoms, especially methyl; and/or
 $R^{15}$ is hydrogen or alkyl; and/or
 $R^{15}$ and $R^4$ taken together form a ring; and/or
 $R^4$ and $R^{12}$ taken together form a ring; and/or
 $R^4$ and $R^{13}$ taken together form a ring;

when Q is phosphorous and Z is nitrogen:
 $R^1$ and $R^2$ are t-butyl; and/or
 $R^8$ is aryl or substituted aryl, especially (VII); and/or
 $R^3$, $R^4$ and $R^5$ are hydrogen, hydrocarbyl or substituted hydrocarbyl, especially hydrogen; and/or
 $R^6$ is aryl or substituted aryl, more preferably phenyl; and/or
 $R^7$ is benzyl;

when Q is phosphorous and Z is oxygen, and $R^5$ and $R^7$ taken together form a double bond:
 $R^1$ and $R^2$ are t-butyl;
 $R^3$ and $R^4$ are hydrogen; and/or
 $R^6$ is —$OR^9$, —$NR^{10}R^{11}$, alkyl, aryl or substituted aryl; and/or
 $R^9$ is alkyl or aryl, especially alkyl containing 1 to 6 carbon atoms or phenyl, and more preferably methyl; and/or
 $R^{10}$ and $R^{11}$ are each independently aryl or substituted aryl, more preferably both phenyl;\ when Q is phosphorous and Z is oxygen, and $R^7$ is hydrocarbyl or substituted hydrocarbyl:
 $R^1$ and $R^2$ are t-butyl;
 $R^3$, $R^4$, $R^5$, and $R^6$ are hydrogen; and or
 $R^7$ is aryl or substituted aryl.

In many of the above formulas a preferred aryl or substituted aryl group is (VII).

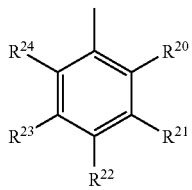

(VII)

In (VII) $R^{20}$, $R^{21}$, $R^{22}$, $R^{23}$ and $R^{24}$ are each independently hydrogen, hydrocarbyl substituted hydrocarbyl or a functional group, provided than any two of $R^{20}$, $R^{21}$, $R^{22}$, $R^{23}$ and $R^{24}$ ortho to another taken together may form a ring. Preferably one of $R^{20}$ and $R^{24}$ is not hydrogen, and more preferably both of $R^{20}$ and $R^{24}$ are not hydrogen. Useful groups for $R^{20}$ and $R^{24}$ include alkyl, especially alkyl containing 1 to 6 carbon atoms, halo especially chloro and bromo, alkoxy, aryl or substituted aryl especially phenyl. Individual useful groups (VII) include 2,6-diisopropylphenyl, 2,6-dimethylphenyl, 2,4,6-trimethylphenyl, 2,6-dimethyl-4-chlorophenyl, and 2,6-dimethyl-4-bromophenyl.

Ligands (I) in which Q is nitrogen may be made by the reaction of a pyruvic (or a pyruvic-like compound which contains a group to be $R^4$ that is something other than methyl) acid ester or amide, or an α,β-dione and an appropriate arylamine. Ligands (I) in which Q is phosphorous and Z is nitrogen may be prepared by the reaction of an appropriate imine with (di-t-butylphosphino)methyl lithium, with subsequent reaction of the lithium amide formed with a halocarbon such as benzyl bromide.

Transition metal complexes having neutral ligands such as (IV) and (IX) can be made by a variety of methods, see for instance previously incorporated U.S. Pat. No. 5,880, 241. In part how such compounds are made depends upon the transition metal compound used in the synthesis of the complex and in what each X (anion) in the final product is. For example, for transition metals such as Ni[II], Fe[II], Co[II], Ti[IV] and Zr[IV] a metal halide such as the chloride may be mixed with the neutral ligand and transition metal complex, wherein X is halide. When it is desired that one of X be a relatively noncoordinating anion and another X is an anion which may add across an olefinic bond (as in ethylene), for example using a nickel compound, then nickel allyl chloride dimer may be mixed with a neutral ligand in the presence of an alkali metal salt of a relatively noncoordinating anion such as sodium tetrakis[3,5-bistrifluoromethylphenyl]borate (BAF for the anion alone) to form a complex in which one X is π-allyl and the other anion BAF.

For the transition metal complexes in which (I) (a neutral ligand) is present preferred transition metals are Pd, Ni, Fe, Co, Ti, Zr, Hf, Sc, V, Cr, and Ru, and especially preferred transition metals are Pd, Ni, Ti, Zr, Fe and Co, and a more preferred transition metals are Ni, Fe, Ti and Zr.

In the first process useful olefins include an olefin of the formula $H_2C=CH(CH_2)_nG$ (VIII), where n is 0 or an integer of 1 or more, g is hydrogen, $-CO_2R^{25}$ or $-C(O)NR^{25}_2$, and each $R^{25}$ is independently hydrogen, or hydrocarbyl substituted hydrocarbyl, styrenes, norbornenes and cyclopentenes. Preferred olefins are when g is hydrogen and n is 0 (ethylene); or g is hydrogen and n is an integer of 1 to 12, especially one (propylene); or g is $-CO_2R^{25}$ wherein $R^{25}$ is alkyl, especially alkyl containing 1 to 6 carbon atoms and more preferably methyl; and when g is $-CO_2R^{25}$, and n is 0 or an integer of 2 to 12. Copolymers may also be prepared.

A preferred copolymer is one containing ethylene and one or more others of (VIII), for example the copolymers ethylene/1-hexene, ethylene/propylene, ethylene/methyl acrylate (n is 0 and $R^{25}$ is methyl), and ethylene/methyl- or ethyl-1-undecylenate.

In (IX) when an olefin may insert between $L^1$ and the transition metal atom, and $L^2$ is an empty coordination site or is a ligand which may be displaced by an olefin, or $L^1$ and $L^2$ taken together are a bidentate monoanionic ligand into which an olefin may inserted between that ligand and the transition metal atom, (IX) may by itself catalyze the polymerization of an olefin. Examples of $L^1$ which form a bond with the metal into which an olefin may insert between it and the transition metal atom are hydrocarbyl and substituted hydrocarbyl, especially phenyl and alkyl, and particularly methyl, hydride, and acyl; and ligands $L^2$ which ethylene may displace include phosphine such as triphenylphosphine, nitrile such as acetonitrile, ether such as ethyl ether, pyridine, and tertiary alkylamines such as TMEDA (N,N,N',N'-tetramethylethylenediamine). Ligands in which $L^1$ and $L^2$ taken together are a bidentate monoanionic ligand into which an olefin may insert between that ligand and the transition metal atom include π-allyl- or π-benzyl-type ligands (in this instance, sometimes it may be necessary to add a neutral Lewis acid cocatalyst such as triphenylborane to initiate the polymerization, see for instance previously incorporated U.S. Pat. No. 5,880,241). For a summary of which ligands ethylene may insert into (between the ligand and transition metal atom) see for instance J. P. Collman, et al., *Principles and Applications of Organotransition Metal Chemistry*, University Science Books, Mill Valley, Calif., 1987.

If for instance $L^1$ is not a ligand into which ethylene may insert between it and the transition metal atom or if (IV) is present, it may be possible to add a cocatalyst which may convert $L^1$ or X into a ligand which will undergo such an insertion. Thus if $L^1$ or X is halide such as chloride or bromide, or carboxylate, it may be converted to hydrocarbyl such as alkyl by use of a suitable alkylating agent such as an alkylaluminum compound, a Grignard reagent or an alkyllithium compound. It may be converted to hydride by using of a compound such as sodium borohydride. It is preferred that when the transition metal is alkylated or hydrided, that a relatively noncoordinating anion is formed. Such reactions are described in previously incorporated U.S. Pat. No. 5,880,241.

A preferred cocatalyst in the first process is an alkylaluminum compound, and useful alkylaluminum compounds include trialkylaluminum compounds such as triethylaluminum, trimethylaluminum and tri-i-butylaluminum, alkyl aluminum halides such as diethylaluminum chloride and ethylaluminum dichloride, and aluminoxanes such as methylaluminoxane.

In another preferred form $L^1$ and $L^2$ taken together may be a π-allyl or π-benzyl group such as

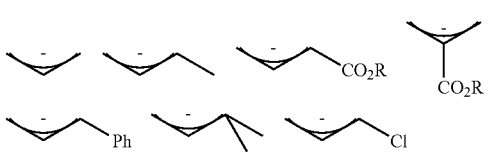

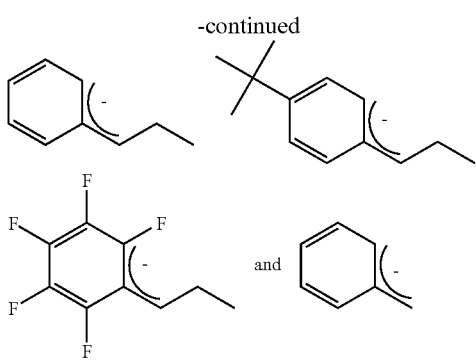

wherein R is hydrocarbyl, and π-allyl and π-benzyl groups are preferred. When $L^1$ and $L^2$ taken together are π-allyl or π-benzyl, in order to initiate the polymerization it may be useful to have a Lewis acid such as triphenylboron or tris(pentafluorophenyl)boron also present.

In the first polymerization process herein, the temperature at which the polymerization is carried out is about −100° C. to about +200° C., preferably about −60° C. to about 170° C., more preferably about −20° C. to about 140° C. The pressure of the ethylene or other gaseous olefin at which the polymerization is carried out is not critical, atmospheric pressure to about 275 MPa being a suitable range.

The first polymerization process herein may be run in the presence of various liquids, particularly aprotic organic liquids. The catalyst system, ethylene or other olefinic monomer, and/or polymer may be soluble or insoluble in these liquids, but obviously these liquids should not prevent the polymerization from occurring. Suitable liquids include alkanes, cycloalkanes, selected halogenated hydrocarbons, and aromatic hydrocarbons. Specific useful solvents include hexane, toluene, benzene, methylene chloride, 1,2,4-trichlorobenzene and p-xylene.

The first polymerization process herein may also initially be carried out in the "solid state" by, for instance, supporting the transition metal compound on a substrate such as silica or alumina, activating if necessary it with one or more cocatalysts and contacting it with, say, ethylene. Alternatively, the support may first be contacted (reacted) with a cocatalysts (if needed) such as an alkylaluminum compound, and then contacted with an appropriate transition metal compound. The support may also be able to take the place of a Lewis or Bronsted acid, for instance an acidic clay such as montmorillonite, if needed. These "heterogeneous" catalysts may be used to catalyze polymerization in the gas phase or the liquid phase. By gas phase is meant that a gaseous olefin is transported to contact with the catalyst particle. In a preferred form of gas phase polymerization the polymerization catalysts and/or polymer formed is in the form of a fluidized bed.

In all of the polymerization processes described herein olefinic oligomers and polymers are made. They may range in molecular weight from oligomeric POs (polyolefins), to lower molecular weight oils and waxes, to higher molecular weight POs. One preferred product is a POs with a degree of polymerization (DP) of about 10 or more, preferably about 40 or more. By "DP" is meant the average number of repeat units in a PO molecule.

Depending on their properties, the POs made by the processes described herein are useful in many ways. For instance if they are thermoplastics, they may be used as molding resins, for extrusion, films, etc. If they are elastomeric, they may be used as elastomers. If they contain functionalized monomers such as acrylate esters or other polar monomers, they are useful for other purposes, see for instance previously incorporated U.S. Pat. No. 5,880,241.

Depending on the first process conditions used and the polymerization catalyst system chosen, the POs may have varying properties. Some of the properties that may change are molecular weight and molecular weight distribution, crystallinity, melting point, and glass transition temperature. Except for molecular weight and molecular weight distribution, branching can affect all the other properties mentioned, and branching may be varied (using the same nickel compound) using methods described in previously incorporated U.S. Pat. No. 5,880,241.

It is known that blends of distinct polymers, that vary for instance in the properties listed above, may have advantageous properties compared to "single" polymers. For instance it is known that polymers with broad or bimodal molecular weight distributions may be melt processed (be shaped) more easily than narrower molecular weight distribution polymers. Thermoplastics such as crystalline polymers may often be toughened by blending with elastomeric polymers.

Therefore, methods of producing polymers which inherently produce polymer blends are useful especially if a later separate (and expensive) polymer mixing step can be avoided. However in such polymerizations one should be aware that two different catalysts may interfere with one another, or interact in such a way as to give a single polymer.

In such a process the transition metal containing polymerization catalyst disclosed herein can be termed the first active polymerization catalyst. A second active polymerization catalyst (and optionally one or more others) is used in conjunction with the first active polymerization catalyst. The second active polymerization catalyst may be another late transition metal catalyst, for example as described in previously incorporated U.S. Pat. No. 5,880,241, U.S. Pat. No. 6,060,569 and U.S. Pat. No. 6,174,795, as well as U.S. Pat. No. 5,714,556 and U.S. Pat. No. 5,955,555 which are also incorporated by reference herein as if fully set forth.

Other useful types of catalysts may also be used for the second active polymerization catalyst. For instance so-called Ziegler-Natta and/or metallocene-type catalysts may also be used. These types of catalysts are well known in the polyolefin field, see for instance *Angew. Chem., Int. Ed. Engl.*, vol. 34, p.1143–1170 (1995), EP-A-0416815 and U.S. Pat. No. 5,198,401 for information about metallocene-type catalysts, and J. Boor Jr., *Ziegler-Natta Catalysts and Polymerizations*, Academic Press, New York, 1979 for information about Ziegler-Natta-type catalysts, all of which are hereby included by reference. Many of the useful polymerization conditions for all of these types of catalysts and the first active polymerization catalysts coincide, so conditions for the polymerizations with first and second active polymerization catalysts are easily accessible. Oftentimes the "cocatalyst" or "activator" is needed for metallocene or Ziegler-Natta-type polymerizations. In many instances the same compound, such as an alkylaluminum compound, may be used as an "activator" for some or all of these various polymerization catalysts.

In one preferred process described herein the first olefin(s) (olefin(s) polymerized by the first active polymerization catalyst) and second olefin(s) (the monomer(s) polymerized by the second active polymerization catalyst) are identical. The second olefin may also be a single olefin or a mixture of olefins to make a copolymer.

In some processes herein the first active polymerization catalyst polymerizes one or olefins, a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer.

Likewise, conditions for such polymerizations, using catalysts of the second active polymerization type, will also be found in the appropriate above mentioned references.

Two chemically different active polymerization catalysts are used in this polymerization process. The first active polymerization catalyst is described in detail above. The second active polymerization catalyst may also meet the limitations of the first active polymerization catalyst, but must be chemically distinct. For instance, it may utilize a different ligand which differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence. Any of the processes applicable to the individual catalysts may be used in this polymerization process with 2 or more catalysts, i.e., gas phase, liquid phase, continuous, etc.

The polymers produced by this process may vary in molecular weight and/or molecular weight distribution and/or melting point and/or level of crystallinity, and/or glass transition temperature and/or other factors. The polymers produced are useful as molding and extrusion resins and in films as for packaging. They may have advantages such as improved melt processing, toughness and improved low temperature properties.

Catalyst components which include transition metal complexes of (I), with or without other materials such as one or more cocatalysts and/or other polymerization catalysts are also disclosed herein. For example, such a catalyst component could include the transition metal complex supported on a support such as alumina, silica, a polymer, magnesium chloride, sodium chloride, etc., with or without other components being present. It may simply be a solution of the transition metal complex, or a slurry of the transition metal complex in a liquid, with or without a support being present.

Hydrogen or other chain transfer agents such as silanes (for example trimethylsilane or triethylsilane) may be used to lower the molecular weight of polyolefin produced in the polymerization process herein. It is preferred that the amount of hydrogen present be about 0.01 to about 50 mole percent of the olefin present, preferably about 1 to about 20 mole percent. The relative concentrations of a gaseous olefin such as ethylene and hydrogen may be regulated by varying their partial pressures.

In the second polymerization process herein, a transition metal complex of Groups 6 to 11, preferably Groups 8–11, more preferably Ni or Pd, and especially preferably Ni, is used. The transition metal is complexed to an "active ligand", and this ligand is bi- or higher (tri-, tetra, etc.) dentate. The ligand may be neutral (have no charge) or anionic (have one or more negative charges). Bidentate ligands are preferred. Besides having this denticity, the active ligand has certain properties, measured by a specific test, that classify it as an active ligand. The ligand may be active with one transition metal but not with another. The complex for any given ligand with each transition metal should be separately tested (see below).

When most such transition metal complexes are used as olefin polymerization catalyst (components), they are usually used in conjunction with other catalyst components, such as alkylating agents, and/or Lewis acids, and/or others. It has been found that these transition metal complexes, when having at least one π-allyl also coordinated to the transition metal, will initiate the polymerization of ethylene, and/or copolymerization of ethylene and ethyl-10-undecylenate, under specified conditions (see below) in the absence of any other cocatalysts. This in a sense makes them especially active in olefin polymerizations, especially polymerizations in which a polar monomer is used (and copolymerized) with a hydrocarbon olefin, especially ethylene.

Generally speaking, these ligands have at least two different types of groups which coordinate to the transition metal, for example two different heteroatom groups such as (in a bidentate ligand) N and O, or N and P, or P and O, etc. In some instances, both the heteroatoms and the groups of which they are a part may be the same. In some instances, the heteroatoms may be same, but the groups of which they are a part are different, for example for nitrogen they may be amino or imino, for oxygen they may be keto or hydroxy, etc. Many of these ligands happen to be so-called "hemilabile" or "hybrid" ligands, although the fact that a ligand is hemilabile or hybrid does not guarantee it will be an active ligand, and vice versa. Hemilabile and hybrid ligands are known in the art, see for instance: J. C. Jeffrey et al., *Inorg. Chem.*, vol. 18, p. 2658 (1979); L. P. Barthel-Rosa, et al., *Inorg. Chem.*, vol. 37, p. 633 (1998); S. Mecking, et al., *Organometallics* vol. 15, p. 2650 (1996); A. M. Allgeier, et al., *Organometallics*, vol. 13, p. 2928 (1994); M. Nandi, M., et al., *J. Am. Chem. Soc.*, vol. 121, p. 9899 (1999); P. Braunstein, et al., *Organometallics*, vol. 15, p. 5551 (1996); A. Bader, et al., *Coord. Chem. Rev.*, vol. 108, p. 27–100 (1991); C. Slone, et al., *In Progress in Inorganic Chemistry*, K. D. Karlin, Ed.; John Wiley & Sons, New York (1999), p. 233–350, all of which are hereby included by reference. Although none of these guides is absolute, they do suggest to the artisan what ligands may be active ligands. Making the transition metal complex and testing it by the simple method described below allows a determination whether the ligand is an active ligand.

When using active ligand complexes to form polar copolymers, preferred hydrocarbon olefins are ethylene and $H_2C=CHR^{26}$, wherein $R^{26}$ is hydrogen, alkyl or substituted alkyl, preferably hydrogen or n-alkyl, and ethylene is especially preferred. A preferred polar olefin is $H_2C=CHR^{27}CO_2R^{28}$, particularly wherein $R^{27}$ is alkylene or a covalent bond, more preferably n-alkylene or a covalent bond, and especially preferably a covalent bond, and $R^{28}$ is hydrocarbyl, substituted hydrocarbyl, or a metal, or any easily derivable functionality such as amide or nitrile, and more preferably $R^{28}$ is hydrocarbyl and substituted hydrocarbyl. Another type of preferred polar olefin is a vinyl olefin wherein the polar group is attached directly to a vinylic carbon atom, for example when $R^{27}$ is a covalent bond. CO may also be used as a polar olefin; however, when CO is present it is preferred that at least one other polar olefin is also present.

In the second process, especially when ethylene is the hydrocarbon olefin, it is preferred that the polymerization process be run at a temperature of about 50° C., more preferably 60° C. to about 170° C., and an ethylene partial pressure of at least about 700 kPa. More preferably the temperature range is about 80° C. to about 140° C. and/or a lower ethylene pressure is about 5.0 MPa or more, and/or a preferred upper limit on ethylene pressure is about 200 MPa, especially preferably about 20 MPa. The polymerizations may otherwise be carried out in the "normal" manner for such ligands (including the presence of Lewis acids, which are not present in part of the test to determine whether a ligand is an active ligand Polymerization without added Lewis acids is described herein in Examples 39–45, 54–58, 70, 73, 91 and 192. Examples of ligands with excellent potential for being active ligands are listed in previously incorporated S. Ittel, et al., *Chem. Rev.*, vol. 100, p. 1177–1179 and are (Reference Numbers from their Table 2 given): 116 E-33; 116 E-32; 116 E-15; 116 E-57; 116 E-51; 116 E-60; 116 E-185; 116 E-23; 116 E-89; 116 E-29; 116 E-27; 116 E-61; 116 E43; 116 E49; 116 E-39; 116 E-56; 116 E-36; 116 E-95; 116 E-3; 116 E-184; 116 E-141; 116 E-144; 116 E-53; 116 E-105; 116 E-106; 116 E-37; 116 E-46; 116 E44; 139; 116 E-10; 116 E-162; 116 E-16; 116 E-48; 116 E-30; 116 E47; 116 E-55; 116 E-24; 116 E-54; 140; 136; 116 E-34; and 116 E-160. From Table 8, p. 1195, 416. Under certain circumstances α-diimines are not preferred neutral active ligands, and/or salicylaldimines are not preferred monoanionic active ligands.

Herein, a ligand is termed an "active ligand" if it meets one or both of the following two tests:

Test 1: The yield of polyethylene obtained under condition 1-1 is greater than or equal to one half of the maximum yield of polyethylene obtained under conditions 1-2 and 1-3.

Conditions 1-1: Heat a clean 600 mL Parr® reactor under vacuum, and then allow it to cool under nitrogen. Next, heat the reactor to 80° C. In a nitrogen-filled drybox, weigh out 0.0085 mmole of the neutral nickel(II) allyl complex [(L^L') Ni(C_3H_5)], the cationic nickel(II) allyl complex [(L^L')Ni (C_3H_5)]^+[B(3,5-(CF_3)_2C_6H_3)_4]^-, or the cationic nickel(II) allyl complex [(L^L')Ni(C_3H_5)]^+[B(C_6F_5)_4]^- and dissolve it in 60 mL of chlorobenzene and then place the solution in a 150 mL addition cylinder. Seal the cylinder and bring it out of the drybox and attach it to the Parr® reactor. Utilize 2.1 MPa of nitrogen to force the solution in the addition cylinder into the 80° C. reactor. Quickly vent the nitrogen and fill the reactor with ethylene to 6.9 MPa. Stir the reaction mixture at 600 rpm while adjusting the temperature of the reaction mixture to 100° C. Maintain the temperature at 100° C. and the pressure at 6.9 MPa while continuing to stir for a total of 1 h. Remove the heat source and vent the ethylene. Back-fill with 0.7 MPa nitrogen and vent the nitrogen after brief stirring. Repeat this two more times. Pour the room temperature mixture into 500 mL methanol, filter, and wash with methanol. Blend the resulting polymer with methanol, filter, and wash with methanol. Repeat this blending/washing procedure two more times, and dry the polymer in vacuo overnight.

Condition 1-2: Repeat the procedure of Condition 1-1, except include 10 equiv of BPh_3 in the addition funnel.

Condition 1-3: Repeat the procedure of Condition 1-1, except include 10 equiv of B(C_6F_5)_3 in the addition funnel.

Test 2: The yield of E/E-10-U copolymer obtained under Condition 1-4 is greater than or equal to one third of the maximum yield of polyethylene obtained under Conditions 1-5 and 1-6.

Condition 1-4: Heat a clean 600 mL Parr® reactor under vacuum, and then allow it to cool under nitrogen. In a nitrogen-filled drybox, weigh out 0.0094 mmole of the neutral nickel(II) allyl complex [(L^L')Ni(C_3H_5)], the cationic nickel(II) allyl complex [(L^L')Ni(C_3H_5)]^+[B(3,5-(CF_3)_2C_6H_3)_4]^-, or the cationic nickel(II) allyl complex [(L^L')Ni(C_3H_5)]^+[B(C_6F_5)_4]^- and dissolve it in 90 mL of toluene and 60 mL of E-10-U in a 300 mL RB flask. Seal the flask with a rubber septum and bring it out of the drybox and transfer the solution into the autoclave via a cannula under positive nitrogen pressure. Seal the autoclave and pressure it to 0.7 MPa nitrogen. Then release the nitrogen. Repeat this pressurizing/venting procedure two more times. Add about 0.03 MPa of nitrogen to the autoclave and then stir the reaction mixture at 600 rpm. Next, apply 4.5 MPa of ethylene pressure. Quickly place the autoclave in a preheated 100° C. oil bath. Adjust the pressure of the autoclave to 5.5 MPa. Maintain the temperature at 100° C. and the pressure at 5.5 MPa while continuing to stir for a total of 2 h. Remove the heat source and vent the ethylene. Back-fill with 0.7 MPa nitrogen and vent the nitrogen after brief stirring. Repeat this two more times. Pour the room temperature mixture into 500 mL methanol, filter, and wash with methanol. Blend the resulting polymer with methanol, filter, and wash with methanol. Repeat this blending/washing procedure two more times, and dry the polymer in vacuo overnight.

Condition 1-5: Repeat the procedure of Conditions 1-4, except include 80 equiv of BPh_3 in the RB flask.

Condition 1-6: Repeat the procedure of Conditions 1-4, except include 80 equiv of B(C_6F_5)_3 in the RB flask.

Test 1:

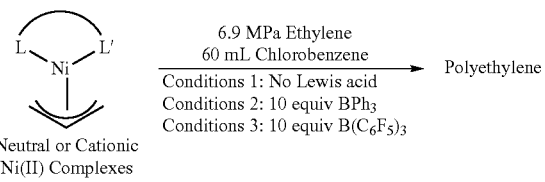

Test 2:

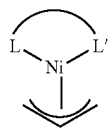

Neutral or Cationic
Ni(II) Complexes

-continued 5.5 MPa Ethylene
60 mL E-10-U
90 mL Toluene
Conditions 4: No Lewis acid
Conditions 5: 80 equiv BPh$_3$
Conditions 6: 80 equiv B(C$_6$F$_5$)$_3$ → E/E-10-U Copolymer In the tests above for "active Ligands" L^L' is bidentate ligand being tested, and E-10-U is ethyl 10-undecylenate. Preferred active ligands are those that meet the conditions for Test 2.

In the Examples except where noted, all pressures are gauge pressures. In the Examples, the following abbreviations are used:

Am—amyl
Ar—aryl
BAF—B(3,5-C$_6$H$_3$—(CF$_3$)$_2$)$_4$$^-$
BArF—B(C$_6$F$_5$)$_4$$^-$
BHT—2,6-di-t-butyl-4-methylphenol
BQ—1,4-benzoquinone
Bu—butyl
Bu$_2$O—dibutyl ether
CB—chlorobenzene
Cmpd—compound
Cy—cyclohexyl
DSC—Differential Scanning Calorimetry
E—ethylene
E-10-U—ethyl-10-undecylenate
EG—end-group, refers to the ester group of the acrylate being located in an unsaturated end group of the ethylene copolymer
EGPEA—2-phenoxyethyl acrylate
Eoc—end-of-chain
Equiv—equivalent
Et—ethyl
Et$_2$O—diethyl ether
GPC—gel permeation chromatography
HA—hexyl acrylate
Hex—hexyl
IC—in-chain, refers to the ester group of the acrylate being bound to the main-chain of the ethylene copolymer
Incorp—incorporation
i-Pr—isopropyl
LA—Lewis acid
LDA—lithium N,N-diethylamide
M.W.—molecular weight
MA—methyl acrylate
Me—methyl
MeOH—methanol
Ml—melt index
Mn—number average molecular weight
Mp—peak molecular weight (by GPC)
Mw—weight average molecular weight
Nd—not determined
PDI—Mw/Mn
PE—polyethylene
Ph—phenyl
PMAO-IP—poly(methylaluminoxane) available from Akzo-Nobel, Inc.
PPA—2,2,3,3,3-pentafluoropropyl acrylate
Press—pressure
RB—round-bottomed
RI—refractive index
RT or Rt—room temperature
t-Bu—t-butyl
TCB—1,2,4-trichlorobenzene
Temp: Temperature
THA—3,5,5-trimethylhexyl acrylate
THF—tetrahydrofuran
TLC—thin layer chromatography
TON—turnovers, moles of olefinic compound polymerized/mole of transition metal compound
Total Me—total number of methyl groups per 1000 methylene groups as determined by 1H or 13C NMR analysis
UV—ultraviolet All the operations related to the catalyst (transition metal compound) synthesis were performed in a nitrogen drybox or using a Schlenk line with nitrogen protection. Anhydrous solvents were used. Solvents were distilled from drying agents under nitrogen using standard procedures: tetrahydrofuran (THF), from sodium benzophenone ketyl. Ni(II) allyl chloride (or bromide) was prepared according to the literature.

(t-Butyl)$_2$PCH$_2$Li was synthesized by reacting (t-butyl)$_2$PCH$_3$ with t-butyl lithium in heptane in a 109° C. bath for 4 d. The product was filtered and washed with pentane. (t-Butyl)$_2$PLi was synthesized by reacting (t-butyl)$_2$PH with n-butyl lithium in heptane at 90° C. for 6 h.

The $^1$H, $^{13}$C and $^{31}$P NMR spectra were recorded using a Bruker 500 MHz spectrometer.

Total methyls per 1000 CH$_2$ are measured using different NMR resonances in $^1$H and $^{13}$C NMR spectra. Because of accidental overlaps of peaks and different methods of correcting the calculations, the values measured by $^1$H and $^{13}$C NMR spectroscopy will not be exactly the same, but they will be close, normally within 10–20% at low levels of acrylate comonomer. In $^{13}$C NMR spectra, the total methyls per 1000 CH$_2$ are the sums of the 1B$_1$, 1B$_2$, 1B$_3$, and 1B$_{4+}$, EOC resonances per 1000 CH$_2$, where the CH$_2$'s do not include the CH$_2$'s in the alcohol portions of the ester group. The total methyls measured by $^{13}$C NMR spectroscopy do not include the minor amounts of methyls from the methyl vinyl ends nor the methyls in the alcohol portion of the ester group. In $^1$H NMR spectra, the total methyls are measured from the integration of the resonances from 0.6 to 1.08 ppm and the CH$_2$'s are determined from the integral of the region from 1.08 to 2.49 ppm. It is assumed that there is 1 methine for every methyl group, and ⅓ of the methyl integral is subtracted from the methylene integral to remove the methine contribution. The methyl and methylene integrals are also usually corrected to exclude the values of the methyls and methylenes in the alcohol portion of the ester group, if this is practical. Because of the low levels of incorporation, this is usually a minor correction. Corrections are also made to exclude any contributions from acrylate homopolymer to the methyl or methylene integrals in both the $^{13}$C and $^1$H spectra where this is warranted.

In the Examples the following ligands and transition metal compounds are made by the general indicated methods. Ligand and transition metal compound numbers are shown in the various synthetic equations.

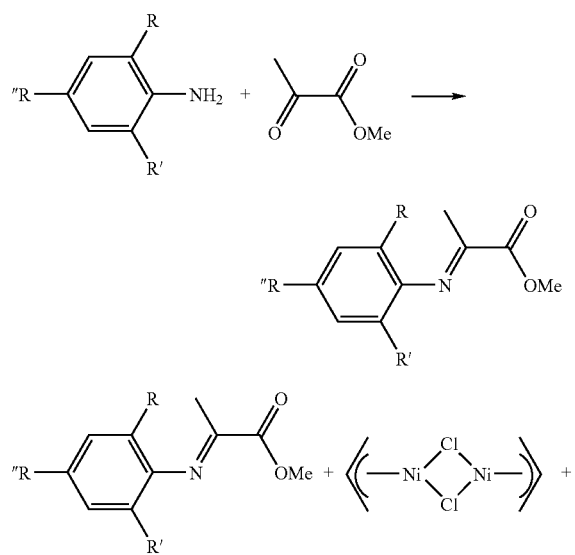
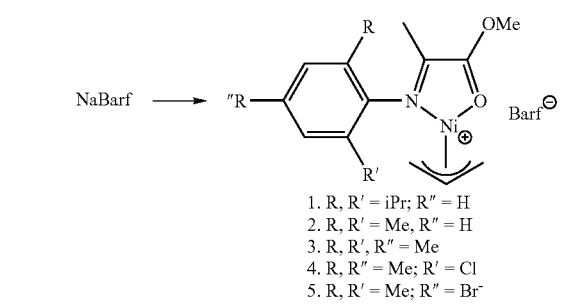
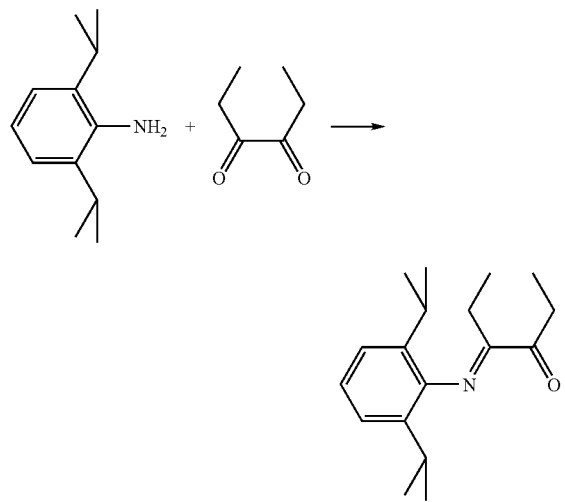
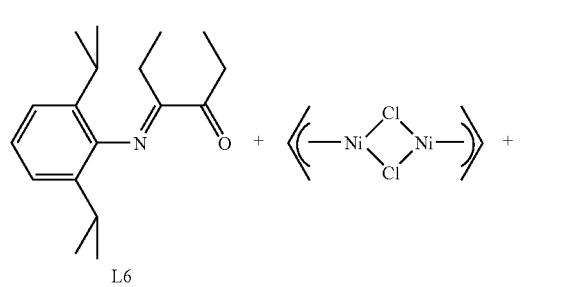
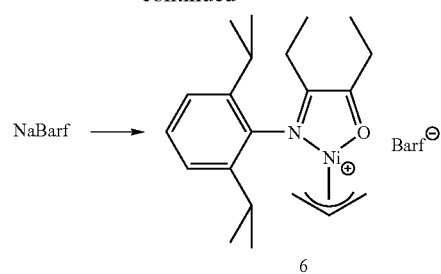
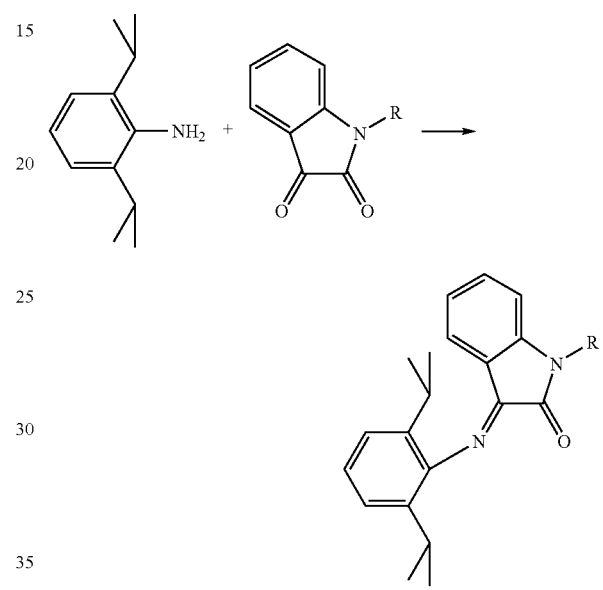
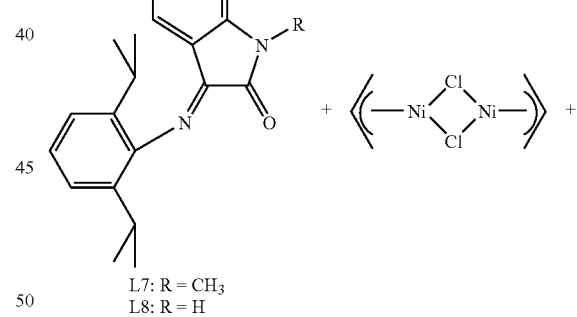
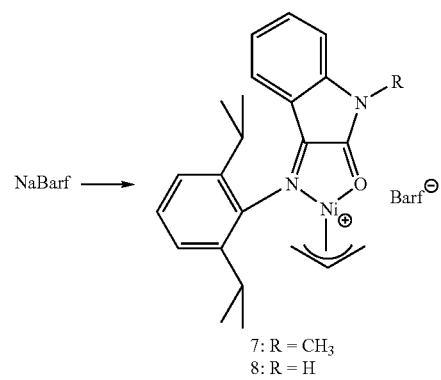

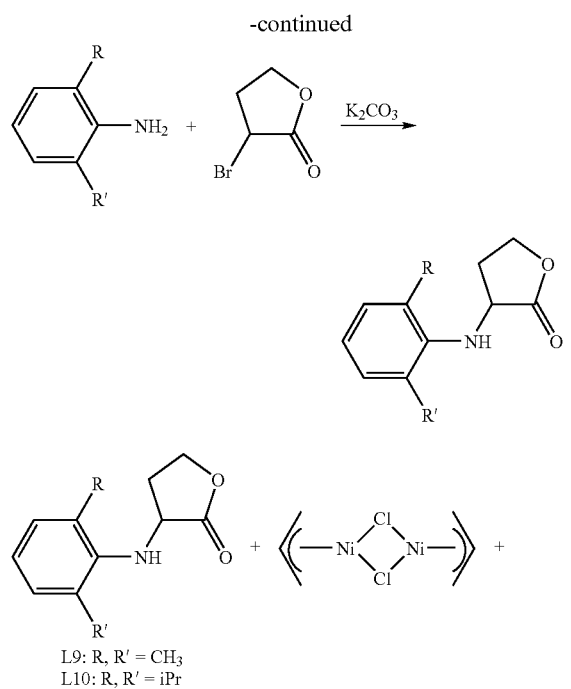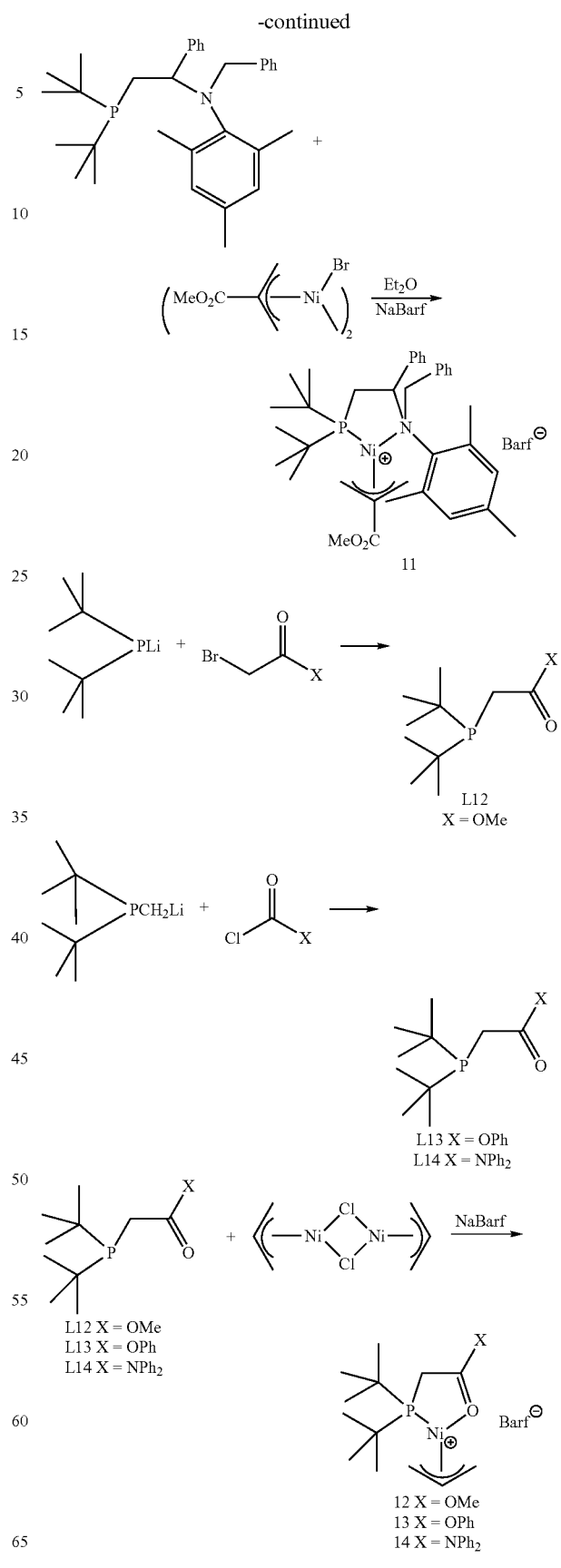

EXAMPLE 1

Synthesis of Ligand L1

In a 300 mL RB flask, 5.672 g (0.05 mole) methyl pyruvate and 9.849 g (0.05 mole) 2,6-diisopropylaniline were mixed with 150 mL toluene and 30 mg (catalytic amount) of p-toluenesulfonic acid monohydrate. A Dean-Stark trap and a reflux condenser were attached to the flask. The yellow solution was refluxed for 4.5 h. Solvent was removed under vacuum. The resulting oil was dissolved in 100 mL hexanes and the solution was cooled at −40° C. overnight. The viscous oil was filtered cold using a cold, coarse filter and was washed with 4×15 mL cold hexanes. The yellow oil was dried in vacuo for 2 h. It weighed 0.619 g. The filtrate was evaporated. The resulting oil was dissolved in 100 mL hexanes. The solution was cooled at −40° C. overnight. Hexanes were decanted. The sample was dried in vacuo for 2 h. The weight of the yellow oil was is 4.172 g (37% overall yield). $^1$HNMR (in $CD_2Cl_2$): δ 7.07–7.18 (m, 3H, Ar—H); 3.92 (s, 3H, —$OCH_3$); 2.63 (heptet, 2H, —$CH(CH_3)_2$); 1.93 (s, 3H, N=C—$CH_3$); 1.11–1.15 (dd, 12H, $(CH_3)_2CH$—).

EXAMPLE 2

Synthesis of Catalyst 1

In a drybox, 0.586 g (2.241 mmol) ligand L1, 0.303 g (1.120 mmol) nickel allyl chloride dimer, 1.986 g (2.241 mmol) sodium tetrakis(3,5-trifluoromethylphenyl)borate and 25 mL diethyl ether were mixed in a 100 mL RB flask. The resulting burgundy mixture was stirred at RT for 2 h. The mixture was then filtered through Celite®, followed by 3×10 mL ether wash. The filtrate was evaporated under vacuum. The residue was dissolved in 3 mL dichloromethane, followed by addition of 30 mL pentane. Solvent was decanted. The procedure was repeated two more times by using 15 mL pentane. The resulting residue was dried under full vacuum. The brown solid was triturated with 20 mL pentane, filtered and washed with 3×10 mL pentane. The product was dried in vacuo for 2 h. Final weight of the brown solid was 2.475 g (90%). $^1$HNMR (in $CD_2Cl_2$): δ 7.72 (s, 8H, Barf-H); 7.57 (s, 4H, Barf-H); 7.26–7.41 (m, 3H, Ar—H); 5.90 (heptet, 1H, central allyl-H); 4.25 (s, 3H, —$OCH_3$); 2.34, 2.81, 3.10, 3.97 (bs, 1H each, terminal allyl-H); 2.66 (heptet, 2H, —$CH(CH_3)_2$); 2.04 (s, 3H, N=C—$CH_3$); 1.04–1.43 (bs, 12H, $(CH_3)_2CH$—).

EXAMPLE 3

Synthesis of Ligand L2

In a 300 mL RB flask, 5.672 g (0.05 mol) methyl pyruvate and 6.061 g (0.05 mol) 2,6-dimethylaniline were mixed with 150 mL toluene and 50 mg p-toluenesulfonic acid monohydrate. A Dean-Stark trap and a reflux condenser were attached to the flask. The amber solution was refluxed for 4 h, at which time ca. 0.9 mL $H_2O$ had been collected. The solution was refluxed for an additional 3 h. Solvent was removed under vacuum. Amber oil was obtained. The oil was dissolved 100 mL hexanes and the solution was cooled at −40° C. overnight. Solvent was decanted. The dark red oil was washed with 3×25 mL cold hexanes. The product was dried in vacuo for 2 h. Final weight of the dark red oil was 3.532 g (34%). $^1$HNMR (in $CD_2Cl_2$): δ 6.90–7.10 (m, 3H, Ar—H); 3.91 (s, 3H, —$OCH_3$); 1.97 [s, 6H, —$C_6H_3(CH_3)_2$]; 1.89 (s, 3H, N=C—$CH_3$).

EXAMPLE 4

Synthesis of Catalyst 2

In a drybox, 0.500 g (2.436 mmol) ligand L2, 0.329 g (1.218 mmol) nickel allyl chloride dimer, 2.159 g (2.436 mmol) sodium tetrakis(3,5-trifluoromethylphenyl)borate and 25 mL diethyl ether were mixed in a 100 mL RB flask. The mixture was stirred at RT for 2 h. It was then filtered through Celite®, followed by 3×10 mL ether wash. The filtrate was evaporated under vacuum. The resulting brown solid was triturated with 20 mL pentane. The solid was filtered and washed with 3×10 mL pentane. The brown solid was dried in vacuo for 2 h. Final weight of the brown solid was 2.300 g (81%). $^1$HNMR (in $CD_2Cl_2$): δ 7.73 (s, 8H, Barf-H); 7.57 (s, 4H, Barf-H); 6.90–7.30 (m, 3H, Ar—H); 5.91 (heptet, 1H, central allyl-H); 4.24 (s, 3H, —$OCH_3$); 1.21, 2.55, 3.60 (bs, total 4H, terminal allyl-H); 2.21 [bs, 6H, —$C_6H_3(CH_3)_2$]; 1.99 (s, 3H, N=C—$CH_3$).

EXAMPLE 5

Synthesis of Ligand L3

In a 300 mL RB flask, 5.672 g (0.05 mol) methyl pyruvate and 6.761 g (0.05 mol) 2,4,6-trimethylaniline were mixed with 150 mL toluene and 50 mg p-toluenesulfonic acid monohydrate. A Dean-Stark trap and a reflux condenser were attached to the flask. The amber solution was refluxed for 4 h, at which time ca. 0.9 mL $H_2O$ had been collected. The solution was refluxed for an additional 3 h. Solvent was removed with a rotary evaporator. The amber oil was dissolved in 100 mL hexanes. The solution was cooled at −40° C. overnight. The hexanes layer was decanted. The dark red oil was washed with 3×25 mL cold hexanes. The product was dried in vacuo for 2 h. Final weight of the dark red oil was 5.574 g (51%). $^1$HNMR (in $CD_2Cl_2$): δ 6.87 (s, 2H, Ar—H); 3.90 (s, 3H, —$OCH_3$); 1.97 [s, 6H, ortho-$C_6H_2(CH_3)_3$]; 2.26, 1.88 [s, 3H each, N=C—$CH_3$ and para-$C_6H_2(CH_3)_3$].

EXAMPLE 6

Synthesis of Catalyst 3

In a drybox, 0.500 g (2.28 mmol) ligand L3, 0.308 g (1.14 mmol) nickel allyl chloride dimer, 2.021 g (2.28 mmol) sodium tetrakis(3,5-trifluoromethylphenyl)borate and 25 mL diethyl ether were mixed in a 100 mL RB flask. The mixture was allowed to stir at RT for 2 h. The mixture was then filtered through Celite®, followed by 3×10 mL ether wash. The filtrate was evaporated under vacuum. The resulting brown solid was triturated with 20 mL pentane. The solid was filtered and washed with 3×10 mL pentane. It was dried in vacuo for 2 h. Final weight of the brown solid was 0.830 g (31%). $^1$HNMR (in $CD_2Cl_2$): δ 7.72 (s, 8H, Barf-H); 7.56 (s, 4H, Barf-H); 6.99 (s, 2H, Ar—H); 5.91 (heptet,1H, central allyl-H); 4.24 (s, 3H, —$OCH_3$); 1.17, 2.25, 2.55, 3.48 (bs, total 4H, terminal allyl-H); 2.17 [bs, 6H, $C_6H_2(CH_3)_3$]; 1.98, 2.30 [s, 3H each, N=C—$CH_3$ and para-$C_6H_2(CH_3)_3$].

EXAMPLE 7

Synthesis of Ligand L4

In a 300 mL RB flask, 5.672 g (0.0482 mol) methyl pyruvate and 7.5 g (0.0482 mol) 2-chloro4,6-dimethylaniline were mixed with 150 mL toluene and 50 mg p-toluenesulfonic acid monohydrate. A Dean-Stark trap and a reflux condenser were attached to the flask. The mixture was refluxed for 6 h. Solvent was removed under vacuum. The residue was dissolved in 100 mL hexanes and the mixture was cooled at −40° C. overnight. The hexanes layer was decanted. The residue was washed with 3×25 mL cold hexanes. It was then dried in vacuo for 2 h. Final weight of the brown-yellow solid/liquid mixture was 8.880 g (77%).

EXAMPLE 8

Synthesis of Catalyst 4

In a drybox, 1.000 g ligand L4, 0.282 g nickel allyl chloride dimer, 1.849 g sodium tetrakis(3,5-trifluoromethylphenyl)borate and 25 mL diethyl ether were mixed in a 100 mL RB flask. The mixture was allowed to stir at RT for 2 h. The mixture was then filtered through Celite®, followed by 3×10 mL ether wash. The filtrate was evaporated under vacuum. The resulting brown solid was triturated with 20 mL pentane. The solid was filtered and washed with 3×10 mL pentane. It was dried in vacuo for 2 h. Final weight of the brown solid was 2.707 g.

EXAMPLE 9

Synthesis of Ligand L5

In a 300 mL RB flask, 5.469 g (0.05 mol) methyl pyruvate and 10.005 g (0.05 mol) 4-bromo-2,6-dimethylaniline were mixed with 150 mL toluene and 50 mg p-toluenesulfonic acid monohydrate. A Dean-Stark trap and a reflux condenser were attached to the flask. The solution was refluxed for 8 h. Solvent was removed under vacuum. The residue was dissolved in 100 mL hexanes and the solution was cooled at −40° C. overnight. Solvent was decanted. The residue was washed with 3×25 mL cold hexanes. The product was dried in vacuo for 2 h. Final weight of the dark red-brown solid/liquid mixture was 8.611 g (61%).

EXAMPLE 10

Synthesis of Catalyst 5

In a drybox, 0.500 g (1.76 mmol) ligand L5, 0.238 g (0.88 mmol) nickel allyl chloride dimer, 1.560 g (1.76 mmol) sodium tetrakis(3,5-trifluoromethylphenyl)borate and 25 mL diethyl ether were mixed in a 100 mL RB flask. The mixture was allowed to stir at RT for 2 h. It was then concentrated to ca. 5 mL and was added 25 mL pentane. Solvent was decanted after brief stirring. The solid was washed with 2×15 mL pentane and was dried in vacuo. Dark brown solid was isolated. Final weight was 1.118 g (51%).

EXAMPLE 11

Synthesis of Ligand L6

In a 300 mL RB flask, 11.738 g (0.103 mol) 3,4-hexanedione, 19.74 g (0.100 mol) 2,6-diisopropylaniline and 8–10 drops of formic acid were mixed with 100 mL methanol. The yellow solution was refluxed for 14 h. It was then cooled at −40° C. overnight. The yellow solid was filtered through a cold, coarse funnel, followed by 4×15 mL cold methanol wash. It was dried in vacuo overnight. Final weight of the yellow solid was 14.016 g (51%). $^1$HNMR (in CD$_2$Cl$_2$): δ 7.05–7.17 (m, 3H, Ar—H); 2.59 (heptet, 2H, —CH(CH$_3$)$_2$); 2.25, 3.03 (q, 2H each, —CH$_2$CH$_3$); 1.18 [d, $^3$J=7.0 Hz, 6H, —CH(CH$_3$)$_2$]; 1.10 [d, $^3$J=6.8 Hz, 6H, —CH(CH$_3$)$_2$]; 0.90, 1.15 (t, 3H each, —CH$_2$CH$_3$).

EXAMPLE 12

Synthesis of Catalyst 6

In a drybox, 0.547 g (2 mmol) ligand L6, 0.270 g (1 mmol) nickel allyl chloride dimer, 1.772 g (2 mmol) sodium tetrakis(3,5-trifluoromethylphenyl)borate and 30 mL diethyl ether were mixed in a 100 mL RB flask. The dark burgundy reaction was allowed to stir at RT for 1.5 h. Solvent was evaporated. The residue was dissolved in 25 mL dichloromethane and the mixture was filtered through Celite®, followed by 4×10 mL dichloromethane wash. The filtrate was evaporated to ca. 2–3 mL and was added 30 mL pentane. Upon brief stirring, the mixture was filtered, followed by 3×10 mL pentane wash of the solid. The solid product was dried in vacuo for 1 h. Final weight of the brick red solid was 2.335 g (94%). $^1$HNMR (in CD$_2$Cl$_2$): δ 7.72 (s, 8H, Barf-H); 7.56 (s, 4H, Barf-H); 7.28–7.41 (m, 3H, Ar—H); 5.88 (heptet, 1H, central allyl-H); 4.00–4.40, 2.00–3.20 [bm, 6H total, terminal allyl-H and —CH(CH$_3$)$_2$]; 3.11, 2.47 (q, 2H each, —CH$_2$CH$_3$); 1.21, 1.32 [d, $^3$J=6.6 Hz, 6H each, —CH(CH$_3$)$_2$]; 1.15, 1.34 (t, 3H each, —CH$_2$CH$_3$).

EXAMPLE 13

Synthesis of Ligand L7

In a 100 mL RB flask, 3.223 g (20 mmol) 1-methylisatin and 3.948 g (20 mmol) 2,6-diisopropylaniline were mixed with 50 mL toluene and 50 mg p-toluenesulfonic acid monohydrate. A Dean-Stark trap and a reflux condenser were attached to the flask. The orange-red solution was refluxed for 8 h. Solvent was removed under reduced vacuum. Upon sitting at RT, orange-red crystals began to grow in the thick, oily residue. It was triturated with ca. 15 mL hexanes. The solid was filtered, followed by 3×15 mL hexanes wash. The orange solid was dried in vacuo overnight. Its final weight was 5.372 g (84%). $^1$HNMR (in CD$_2$Cl$_2$): δ 6.20 –7.40 (total 7H, Ar—H); 3.28 (s, 3H, —NCH$_3$); 2.75 (heptet, 2H, —CH(CH$_3$)$_2$); 0.96, 1.15 (d, $^3$J=6.8 Hz, 6H each, —CH(CH$_3$)$_2$).

EXAMPLE 14

Synthesis of Catalyst 7

In a drybox, 0.641 g (2 mmol) ligand L7, 0.270 g (1 mmol) nickel allyl chloride dimer, 1.772 g (2 mmol) sodium tetrakis(3,5-trifluoromethylphenyl)borate and 25 mL diethyl ether were mixed in a 100 mL RB flask. The dark burgundy solution was stirred at RT for 3 h. The mixture was then filtered through Celite®, followed by 3×10 mL ether wash. The filtrate was evaporated under full vacuum. Final weight of the dark brown foamy solid was 2.412 g (94%).

EXAMPLE 15

Synthesis of Ligand L8

In a 300 mL RB flask, 2.943 g (20 mmol) isatin and 3.948 g (20 mmol) 2,6-diisopropylaniline were mixed with 150 mL toluene and 50 mg p-toluenesulfonic acid monohydrate.

A Dean-Stark trap and a reflux condenser were attached to the flask. The orange-red solution was refluxed for 8 h. Upon cooling to RT, solid was formed in the flask. It was filtered, followed by 3×25 mL hexanes wash. The product was dried in vacuo overnight. Final weight of the golden yellow solid was 4.778 g (78%). $^1$HNMR (in $CD_2Cl_2$): δ 7.98 (s, 1H, —NH); 6.20–7.34 (total 7H, Ar—H); 2.76 (heptet, 2H, —$CH(CH_3)_2$); 0.97, 1.15 (d, $^3J$=6.9 Hz, 6H each, —CH$(CH_3)_2$).

EXAMPLE 16

Synthesis of Catalyst 8

In a drybox, 0.613 g (2 mmol) ligand L8, 0.270 g (1 mmol) nickel allyl chloride dimer, 1.772 g (2 mmol) sodium tetrakis(3,5-trifluoromethylphenyl)borate and 25 mL diethyl ether were mixed in a 100 mL RB flask. The dark red solution was stirred at RT for 3 h. The mixture was then filtered through Celite®, followed by 3×10 mL ether wash. The residue was dissolved in ca. 3 mL dichloromethane, followed by addition of 30 mL pentane. Upon brief stirring, solvent was decanted. The residue was washed with 2×20 mL pentane. It was dried under full vacuum for 2 h. Final weight of the red-tinted, dark brown solid was 2.289 g (90%).

EXAMPLE 17

Synthesis of Ligand L9

In a 100 mL RB flask, 4.920 g (40.6 mmol) 2,6-dimethylaniline, 8.394 g (50.75 mmol) α-bromo-γ-butyrolactone, 2.582 g (24.36 mmol) sodium carbonate and 50 mL xylenes were mixed. A Dean-Stark trap and a reflux condenser were attached to the flask. The mixture was refluxed for 5 h. Water (100 mL) was used to work up the reaction. The organic layer was separated and was washed with 100 mL 5% HCl, followed by a 100 mL brine wash. The organic layer was isolated and was dried over $MgSO_4$. The solution was filtered. Solvent was removed under reduced vacuum. The resulting oil was adhered to silica gel (50 g) and was performed a filtergraph by using 100% dichloromethane as eluent. The appropriate fraction was collected (based on TLC). Solvent was evaporated under full vacuum. Amber oil was obtained. It crystallized upon standing at RT. Final weight of the light tan solid was 0.800 g (10%).

$^1$HNMR (in $CDCl_3$): δ 7.04 (d, $^3J$=7.5 Hz, 2H, meta-Ar—H); 6.91 (t, 1H, para-Ar—H); 4.43 (vt, 1H, —NH-$CHCO_2$—); 3.98, 4.20 [m, 1H each, —CHH'OC(O)—]; 3.55 (s, 1H, —NH); 2.37 [s, 6H, —$C_6H_3(CH_3)_2$]; 2.25, 2.64 [m, 1H each, —CHH'$CH_2$OC(O)—].

EXAMPLE 18

Synthesis of Catalyst 9

In a drybox, 0.800 g (3.898 mmol) ligand L9, 0.527 g (1.949 mmol) nickel allyl chloride dimer, 3.454 g (3.898 mmol) sodium tetrakis(3,5-trifluoromethylphenyl)borate and 25 mL diethyl ether were mixed in a 100 mL RB flask. The resulting deep burgundy mixture was stirred at RT for 1.5 h. The mixture was then filtered through Celite®, followed by 3×10 mL ether wash. The filtrate was evaporated under full vacuum. The residue was dissolved in ca. 3 mL dichloromethane and was added 30 mL pentane. Upon brief stirring, solvent was decanted. The residue was washed with 2×25 mL pentane. Solid precipitated out during the final pentane wash. It was filtered, followed by 3×15 mL pentane wash. The product was dried in vacuo for 3.5 h. Final weight of the tan-pale orange solid was 2.066 g (45%).

EXAMPLE 19

Synthesis of Ligand L10

In a 100 mL RB flask, 5.123 g (26.02 mmol) 2,6-diisopropylaniline, 5.358 g (32.525 mmol) α-bromo-γ-butyrolactone, 1.655 g (15.612 mmol) sodium carbonate and 50 mL xylenes were mixed. A Dean-Stark trap and a reflux condenser were attached to the flask. The mixture was refluxed for 12 h. Water (100 mL) was used to work up the reaction. The organic layer was separated and was washed with 100 mL 5% HCl, followed by a 100 mL brine wash. The organic layer was isolated and was dried over $Na_2SO_4$. The solution was filtered. Solvent was evaporated under reduced vacuum. The resulting oil was adhered to silica gel (50 g) and a filtergraph was performed by using 4:1 hexanes/ethyl acetate as eluent. The appropriate fraction (based on TLC) was collected. Solvent was evaporated under full vacuum. Viscous amber oil was obtained. It crystallized upon standing at RT. Final weight of the light tan solid was 0.770 g (11%). $^1$HNMR (in $CDCl_3$): δ 7.15 (m, 3H, Ar—H); 4.43 (vt, 1H, —$NHCHCO_2$—); 3.80, 4.17 [m, 1H each, —CHH'OC(O)—]; 3.56 (s, 1H, —NH); 3.45 [heptet, 2H, —$CH(CH_3)_2$]; 2.31, 2.53 [m, 1H each, —CHH'$CH_2$OC(O)—], 1.26 [dd, 12H, —$CH(CH_3)_2$].

EXAMPLE 20

Synthesis of Catalyst 10

In a drybox, 0.523 g (2 mmol) ligand L10, 0.270 g (1 mmol) nickel allyl chloride dimer, 1.772 g (2 mmol) sodium tetrakis(3,5-trifluoromethylphenyl)borate and 25 mL diethyl ether were mixed in a 100 mL RB flask. The resulting burgundy mixture was stirred at RT for 3.5 h. The mixture was then filtered through Celite®, followed by 3×10 mL ether wash. The filtrate was evaporated under full vacuum. The residue was dissolved in ca. 3 mL dichloromethane and was added 30 mL pentane. Upon brief stirring, solvent was decanted. The residue was washed with 2×25 mL pentane. Solid precipitated out (upon the scratching of the glass) during the final pentane wash. The solid was filtered and was washed with 3×15 mL pentane. It was dried in vacuo for 3 h. Final weight of the tan-pale orange solid was 2.412 g (98%). Isomers existed based on $^1$HNMR in THF-$d_8$. The overall integration of the $^1$HNMR peaks was consistent with the proposed structure.

EXAMPLE 21

Synthesis of Ligand L11

At −30° C., to a 100 mL round bottom flask containing 10 mL of THF solution of N-(2,4,6-trimethylphenyl)benzylimine (0.354 g, 1.59 mmol), was added dropwise a solution of $(t-Bu)_2PCH_2Li$ (0.264 g, 1.59 mmol) in 10 mL of THF. The mixture was stirred for one h and it turned greenish yellow. Then the THF solution of benzyl bromide [0.272 g (1.59 mmol) of benzyl bromide in 5 mL THF] was added to the mixture and the reaction mixture was allowed to stir overnight. Solvent was removed under vacuum. The residue was extracted with pentane. After evaporating pentane, colorless crystals (0.310 g, 0.65 mmol) were collected in 41% yield. Both $^1$H NMR and $^{31}$P NMR were complicated. However, the X-ray single crystal structure was consistent with the desired product.

EXAMPLE 22

Synthesis of Catalyst 11

In a 100 mL RB flask, 0.134 g (0.282 mmol) Ligand L11, 0.067 g (0.141 mmol) allyl nickel bromide dimer and 0.250 g (0.282 mmol) sodium tetrakis(3,5-bistrifloromethyl-phenyl)borate were mixed with 30 mL of ether and the mixture was stirred for 1 h. The solution became dark brown and it was filtered through Celite®. Solvent was removed under vacuum. The residue was washed with pentane. Dark green powder (0.360 g) was obtained. $^{31}$PNMR ($C_6D_6$): one major peak at 46.48 ppm.

EXAMPLE 23

Synthesis of Ligand L12

In a drybox, 1.006 g (6.573 mmol) methyl bromoacetate and 40 mL THF were mixed in a 100 mL RB flask. The flask was placed in a freezer at −30° C. for 0.5 h. (t-Bu)$_2$PLi [1.000 g (6.573 mmol)] was added to it. The color of the reaction mixture changed rapidly from yellow to orange. The mixture was allowed to stir at RT overnight. It was then evaporated under full vacuum overnight. Pentane (30 mL) was added to the resulting crystalline residue for trituration. Solid was filtered and was washed with 2×15 mL pentane. It was dried in vacuo for several hours. Final weight of the pale orange solid was 1.233 g (61%).

EXAMPLE 24

Synthesis of Catalyst 12

In a drybox, Ligand L12 (0.5 g, 1.64 mmol), 0.222 g (0.82 mmol) nickel allyl chloride dimer, 1.453 g (1.64 mmol) sodium tetrakis(3,5-trifluoromethylphenyl)borate and 30 mL THF were mixed in a 100 mL RB flask. The burgundy mixture was stirred at RT for 3 h. The mixture was then evaporated under full vacuum. The residue was dissolved in ca. 5 mL dichloromethane and was added ca. 50 mL pentane. The resulting yellow solid was filtered and was washed with 3×10 mL pentane. It was dried in vacuo for several hours. Final weight of the light yellow solid was 1.956 g.

EXAMPLE 25

Synthesis of Ligand L13

In a drybox, 0.471 g (3.01 mmol) phenyl chloroformate and 15 mL THF were mixed in a 100 mL RB flask. It was placed in a freezer at −30° C. for 0.5 h. At the same time, 0.5 g (3.01 mmol) (t-Bu)$_2$PCH$_2$Li was dissolved in 10 mL THF. It was then slowly (dropwise) added to the above cold solution. The reaction mixture was allowed to warm up to RT and stir at this temperature for 1 h. The mixture was evaporated under full vacuum overnight. The residue was extracted with 25 mL toluene. The mixture was filtered through Celite®, followed by 3×10 mL toluene wash. The filtrate was evaporated and the solid was dried in vacuo. Tacky orange solid [0.501 g (59%)] was obtained.

EXAMPLE 26

Synthesis of Catalyst 13

In a drybox, Ligand L13 (0.501 g, 1.786 mmol), 0.242 g (0.893 mmol) nickel allyl chloride dimer, 1.583 g (1.786 mmol) sodium tetrakis(3,5-trifluoromethylphenyl)borate and 25 mL diethyl ether were mixed in a 100 mL RB flask. The mixture was stirred at RT for 2 h. The mixture was then filtered through Celite®, followed by 3×10 mL ether wash. The filtrate was evaporated under full vacuum. The residue was dissolved in ca. 5 mL dichloromethane and was added ca. 50 mL pentane. After brief stirring, solvent was decanted. The residue was washed with 2×25 mL pentane. It was dried under full vacuum for 1 h. Final weight of the tacky dark brown solid was 1.675 g (75%).

EXAMPLE 27

Synthesis of Ligand L14

In a drybox, 0.697 g (3.01 mmol) diphenylcarbamyl chloride and 15 mL THF were mixed in a 100 mL RB flask. It was placed in a freezer at −30° C. for 0.5 h. At the same time, 0.5 g (3.01 mmol) (t-Bu)$_2$PCH$_2$Li was dissolved in 10 mL THF. It was then slowly (dropwise) added to the above cold solution. The dull orange reaction mixture was allowed to warm up to RT and stir at this temperature for 1 h. The mixture was evaporated to dryness. The residue was extracted with 25 mL toluene and was filtered through Celite®, followed by 3×10 mL toluene wash. Solvent was evaporated and the product was dried under full vacuum. Orange-red, viscous oil [0.798 g (75%)] was obtained.

EXAMPLE 28

Synthesis of Catalyst 14

In a drybox, Ligand L14 (0.798 g, 2.246 mmol), 0.304 g (1.123 mmol) nickel allyl chloride dimer, 1.990 g (2.246 mmol) sodium tetrakis(3,5-trifluoromethylphenyl)borate and 25 mL diethyl ether were mixed in a 100 mL RB flask. The mixture was stirred at RT for 2 h. It was then filtered through Celite®, followed by 3×10 mL ether wash. The filtrate was evaporated under full vacuum. The residue was dissolved in ca. 5 mL dichloromethane and was added ca. 50 mL pentane. Solvent was decanted. The residue was washed with 2×25 mL pentane. The final product was dried in vacuo. Dark brown, tacky solid [2.673 g (90%)] was obtained. $^{31}$PNMR (in CD$_2$Cl$_2$): δ 70.13 (s, major peak); 45.58 (s, minor peak). There were also a few very small singlet peaks presented in the spectra. $^1$HNMR of the major product (in CD$_2$Cl$_2$): δ 7.75 (s, 8H, Barf-H); 7.58 (s, 4H, Barf-H); 6.70–7.55 (m, 10H, Ar—H); 5.55 (heptet, 1H, central allyl-H); 4.39 (vd, $^3$J=7.7 Hz, 1H, terminal allyl-H); 3.36, 3.14 (dd, 1H each, terminal allyl-H); 2.63–2.85 (dddd, ABX pattern, X was phosphorus, 2H total, —PCHH'—); 1.93 (d, $^3$J=13.1 Hz, 1H, terminal allyl-H); 1.40, 1.22 (d, $^3$J=14.8 Hz, 9H each, —P(CH$_3$)$_3$].

EXAMPLES 29–32

Synthesis of Catalysts 15–18

General Procedure

In a drybox, 2.28 mmol MX$_n$, 0.5 g (2.28 mmol) ligand L3 and 15 mL THF were mixed in a 20 mL vial. The mixture was stirred at RT overnight. Solvent was evaporated and the product was dried in vacuo overnight.

Catalyst 15, $MX_2=FeCl_2$. Final weight of the dark and tacky solid was 0.914 g.

Catalyst 16, $MX_2=CoCl_2$. Final weight of the turquoise solid was 0.924 g.

Catalyst 17, $MX_n=TiCl_4$. Final weight of the dark solid was 1.499 g.

Catalyst 18, $MX_n=ZrCl_4$. Final weight of the dark solid was 1.551 g.

EXAMPLES 33–36

Synthesis of Catalysts 19–22

General Procedure

In a drybox, 1.56 mmol $MX_n$, 0.5 g (1.56 mmol) ligand L7 and 15 mL THF were mixed in a 20 mL vial. The mixture was stirred at RT overnight. Solvent was evaporated and the product was dried in vacuo overnight.

Catalyst 19, $MX_n=CoCl_2$. Final weight of the dark, foamy solid was 0.841 g.

Catalyst 20, $MX_n=FeCl_2$. Final weight of the dark, foamy solid was 0.854 g.

Catalyst 21, $MX_n=TiCl_4$. Final weight of the dark, foamy solid was 1.040 g.

Catalyst 22, $MX_n=ZrCl_4$. Final weight of the dark, foamy solid was 1.094 g.

EXAMPLES 37–92

Polymerization of Olefinic Compounds

Ethylene Polymerization Screening Using the Nickel Catalysts 1 to 14

In a drybox, a glass insert was loaded with the isolated Ni catalysts. TCB, and optionally comonomers, were added to the glass insert. A Lewis acid cocatalyst (typically $BPh_3$ or $B(C_6F_5)_3$) was often added to the solution. The insert was then capped and sealed. Outside of the drybox, the tube was placed under ethylene and was shaken mechanically at the temperature listed in Table 1 for about 18 h. The resulting reaction mixture was mixed with methanol, filtered, repeatedly washed with methanol and the solid polymer dried in vacuo.

Ethylene Polymerization Screening using Catalysts 15–22, in the Presence of MAO

In a drybox, a glass insert was loaded with 0.02 mmol of the isolated Zr or Ti catalyst and 9 mL of TCB. It was then cooled to −30° C. PMAO-IP [1 mL 12.9 wt % (in Al) toluene solution] was added to the frozen solution. It was put in a −30° C. freezer. The insert was then capped and sealed. Outside of the drybox, the cold tube was placed under ethylene and was shaken mechanically at the temperature listed in Table 1, condition IX, for about 18 h. Methanol (about 15 mL) and 2 mL conc. hydrochloric acid was added to the mixture. The polymer was isolated, washed with methanol several times and dried in vacuo.

Polymer Characterization

The results of ethylene polymerization and copolymerization catalyzed by various catalysts under different reaction conditions (See Table 1) are reported in Tables 2–13. The polymers were characterized by NMR, GPC and DSC analysis. A description of the methods used to analyze the amount and type of branching in polyethylene is given in previously incorporated U.S. Pat. No. 5,880,241. GPC's were run in TCB at 135° C. and calibrated against polyethylene using universal calibration based on polystyrene narrow fraction standards. DSC was recorded between −100° C. to 150° C. at a rate of 10° C./minute. Data reported here are all based on second heat. Melting points are taken as the peak of the melting endotherm. $^1$HNMR of the polymer samples was run in tetrachloroethane-$d_2$ at 120° C. using a 500 MHz Bruker spectrometer.

Table 1 gives general conditions for the various polymerizations. The results of these polymerizations are reported in Tables 2–13.

TABLE 1

Conditions for Olefinic Polymerizations

| | |
|---|---|
| I | 0.02 mmol catalyst, 10 mL TCB, RT, 18 h, 6.9 MPa ethylene |
| II | 0.02 mmol catalyst, 6 mL TCB, 4 mL HA or E-10-U, 100° C., 18 h, 6.9 MPa ethylene, 40 eq $B(C_6F_5)_3$, 20 eq $LiB(C_6F_5)_4$ |
| III | 0.02 mmol catalyst, 10 mL TCB, RT, 18 h, 1.0 MPa ethylene, 10 eq $BPh_3$ |
| IV | 0.02 mmol catalyst, 10 mL TCB, 60° C., 18 h, 1.0 MPa ethylene |
| V | 0.02 mmol catalyst, 10 mL TCB, 60° C., 18 h, 1.0 MPa ethylene, 10 eq $BPh_3$ |
| VI | 0.02 mmol catalyst, 8 mL TCB, 2 mL HA, 100° C., 18 h, 6.9 MPa ethylene, 40 eq $B(C_6F_5)_3$, 20 eq $LiB(C_6F_5)_4$ |
| VII | 0.02 mmol catalyst, 6 mL TCB, 4 mL E-10-U, RT, 18 h, 6.9 MPa ethylene, 40 eq $B(C_6F_5)_3$ |
| VIII | 0.02 mmol catalyst, 10 mL TCB, RT, 18 h, 6.9 MPa ethylene, 10 eq $B(C_6F_5)_3$ |
| IX | 0.02 mmol catalyst, 9 mL TCB, 1 mL PMAO-IP, RT, 18 h, 6.9 MPa ethylene |
| X | 0.00125 mmol catalyst, 6 mL TCB, 4 mL E-10-U, 100° C., 18 h, 6.9 MPa ethylene, 640 eq $BPh_3$ |

TABLE 2

Lewis Acid effect on Ethylene Polymerization by 1, Condition I

| Ex | Cocatalyst/ amt | Yield (g) | #Me/ 1000CH$_2$ | m.p. (° C.) ($\Delta H_f$) | Mw/PDI | TON |
|---|---|---|---|---|---|---|
| 37 | B(C$_6$F$_5$)$_3$/ 10 eq | 10.048 | 40 | 116/103 (114.0) | 21,656/7.58 | 17,910 |
| 38 | BPh$_3$/10 eq | 15.95 | 7 | 132 (154.6) | 104,819/2.30 | 28,430 |
| 39 | none | 7.408 | 9 | 137 (170.4) | 135,105/2.24 | 13,204 |

TABLE 3

Ethylene polymerization Without Lewis Acid, Condition I

| Ex. | Catalyst | Yield (g) | #Me/ 1000CH$_2$ | m.p. (° C.) ($\Delta H_f$) | Mw/PDI | TON |
|---|---|---|---|---|---|---|
| 40 | 1 | 4.561 | 9 | 132 (159.1) | 163,953/2.16 | 8,130 |
| 41 | 2 | 7.207 | 13 | 132 (203.3) | 43,244/5.19 | 12,846 |
| 42 | 3 | 14.336 | 7 | 133 (210.6) | 42,879/6.85 | 25,552 |
| 43 | 4 | 3.99 | 38 | 122 (157.8) | 3,698/5.50 | 7,112 |
| 44 | 5 | 2.868 | 9 | 133 (207.9) | 48,447/5.18 | 5,112 |
| 45 | 12 | 0.460 | 27 | 100 (208.0) | 963/1.82 | 820 |

TABLE 4

Ethylene Copolymerization, Condition II

| Ex | Cat. | Comonomer (Mole %) | Yield (g) | #Me/ 1000CH$_2$ | m.p. (° C.) ($\Delta H_f$) | Mw/PDI | TON E/Comonomer |
|---|---|---|---|---|---|---|---|
| 46 | 1 | HA (2.3) | 0.356[a] | 13 | 122 (138.6) | 4,864/2.6 | 477/11 |
| 47 | 1[b] | E-10-U (9.0) | 20.483 | 32 | 99 (99.0) | 10,137/3.6 | 20,871/2056 |
| 48 | 6 | HA[c] (0.2) | 0.403[d] | 3 | 126 (181.4) | 19,918/8.0 | 659/6 |

[a]Contained 0.302 g copolymer and 0.054 g homopolymer of HA
[b]No LiB(C$_6$F$_5$)$_4$ was added in this case
[c]1 mL HA and 9 mL TCB were used rather than 4 mL HA and 6 mL TCB
[d]Contained 0.380 g copolymer and 0.023 g homopolymer of HA

TABLE 5

Ethylene Polymerization, Condition III

| Ex. | Catalyst | Yield (g) | #Me/1000CH$_2$ | m.p. (° C.) ($\Delta H_f$) | Mw/Mn | TON |
|---|---|---|---|---|---|---|
| 49 | 1 | 0.929 | 7 | 122 (118.4) | 207,144/75,900 | 1,656 |
| 50 | 2 | 3.234 | 15 | 129 (170.0) | 60,021/9,387 | 5,764 |
| 51 | 3 | 2.600 | 10 | 128 (163.6) | 74,417/9,248 | 4,634 |
| 52 | 4 | 5.755 | 95 | 114 (52.0) | 1,786/159 | 10,258 |
| 53 | 5 | 1.813 | 19 | 126 (159.7) | 51,793/8,656 | 3,231 |

TABLE 6

Ethylene Polymerization, Condition IV

| Ex. | Catalyst | Yield (g) | #Me/ 1000CH$_2$ | m.p. (° C.) ($\Delta H_f$) | Mw/PDI | TON |
|---|---|---|---|---|---|---|
| 54 | 1 | 2.715 | 17 | 120 (163.4) | 75,492/3.15 | 4,839 |
| 55 | 2 | 1.875 | 46 | 124 (186.6) | 13,949/3.43 | 3,342 |
| 56 | 3 | 3.780 | 74 | 119 (140.2) | 7,181/5.89 | 6,737 |
| 57 | 4 | 4.061 | 82 | 113 (146.3) | 1,499/4.15 | 7,238 |
| 58 | 5 | 4.387 | 84 | 118 (127.7) | 5,930/4.24 | 7,819 |

TABLE 7

Ethylene Polymerization, Condition V

| Ex. | Catalyst | Yield (g) | #Me/1000CH$_2$ | m.p. (° C.) ($\Delta H_f$) | Mw/Mn | TON |
|---|---|---|---|---|---|---|
| 59 | 1 | 7.344 | 40 | 116 (129.7) | 56,827/20,079 | 13,090 |
| 60 | 2 | 3.017 | 63 | 125 (159.2) | 15,953/3,695 | 5,378 |
| 61 | 3 | 7.020 | 65 | 117 (83.5) | 5,038/1,101 | 12,512 |
| 62 | 4 | 10.934 | 83 | 108 (108.2) | 2,433/310 | 19,489 |
| 63 | 5 | 9.609 | 85 | 115 (77.8) | 4,678/795 | 17,127 |

TABLE 8

Ethylene/HA Copolymerization, Condition VI

| Ex. | Catalyst | Yield (g)[a] | #Me/1000CH$_2$ | Mole % Comonomer | m.p. (° C.) ($\Delta H_f$) | Mw/PDI |
|---|---|---|---|---|---|---|
| 64 | 1 | 1.750 | 27 | 0.8 | 124 (160.1) | 10,049/3.47 |
| 65 | 2 | 1.710 | 26 | 1.2 | 118 (176.1) | 3,422/2.42 |
| 66 | 3 | 0.834 | 34 | 1.8 | 120 (147.9) | 3,605/1,521 |
| 67 | 4 | 0.478 | 52 | 2.2 | 95 (132.9) | 2,392/2.37 |
| 68 | 5 | 0.804 | 36 | 1.8 | 119 (153.5) | 3,275/2.40 |
| 69 | 14[b] | 4.257 | 8 | 1.1 | 123 (158.1) | 7,725/1.97 |

[a]All of the copolymer products contained a small amount of homopolymer of HA
[b]20 eq of NaBArF was used here rather than 20 eq of LiB(C$_6$F$_5$)$_4$; toluene was used as solvent here rather than TCB

TABLE 9

Lewis Acid Effect on Ethylene Polymerization by 6, Condition I

| Ex. | Cocatalyst/amt | Yield (g) | #Me/1000CH$_2$ | m.p. (° C.) ($\Delta H_f$) | Mw/PDI | TON |
|---|---|---|---|---|---|---|
| 70 | None | 23.112 | 7 | 134 (169.5) | 267,975/3.45 | 41,195 |
| 71 | BPh$_3$/10 eq | 32.347 | 8 | 135 (166.0) | 260,241/3.15 | 57,655 |
| 72 | B(C$_6$F$_5$)$_3$/10 eq | 27.993 | 6 | 135 (164.2) | 247,973/2.69 | 49,894 |
| 73 | None[a] | 10.716 | 64 | 122 (82.9) | 167,508/3.27[b] | 17,382/573 |

[a]4 mL 1-Hexene and 6 mL TCB was used in this case. Hexene incorporation was 3.19 mole %.
[b]Bimodal, Mp 2,549

TABLE 10

Ethylene/E-10-U Copolymerization, Condition VII

| Ex. | Catalyst | Comonomer Mole % | Yield (g) | #Me/1000CH$_2$ | m.p. (° C.) ($\Delta H_f$) | Mw/PDI | TON E/Comonomer |
|---|---|---|---|---|---|---|---|
| 74 | 6 | 7.4 | 4.532 | 22 | 117 (76.0) | 217,052/3.29[a] | 5,027/403 |

[a]Bimodal, Mp 1,346.

TABLE 11

Ethylene Polymerization, Condition VIII

| Ex. | Catalyst | Yield (g) | #Me/1000CH$_2$ | m.p. (° C.) ($\Delta H_f$) | Mw/PDI | TON |
|---|---|---|---|---|---|---|
| 75 | 7 | 19.181 | 22 | 130 (211.8) | 50,323/5.07 | 34,188 |
| 76 | 9 | 3.534 | 37 | 127 (92.4) | Mn = 2,260[a] | 6,299 |
| 77 | 10 | 5.415 | 22 | 128 (102.2) | Mn = 2,340[a] | 9,652 |
| 78 | 11 | 3.983 | 55 | 120 (156.9) | 13,249/2.94 | 7,099 |
| 79 | 12 | 8.308 | 51 | 94 (123.9) 16 (17.0) | 1,772/4.42[b] | 14,808 |

[a]Based on $^1$HNMR
[b]Bimodal, Mp 267 (minor).

TABLE 12

Ethylene Polymerization, Condition IX

| Ex. | Catalyst | Yield (g) | #Me/1000CH$_2$ | m.p. (° C.) ($\Delta H_f$) | Mn, $^1$HNMR | TON |
|---|---|---|---|---|---|---|
| 80 | 15 | 0.301 | 5 | 131 (157.7) | 4,635 | 537 |
| 81 | 16 | 0.156 | 23 | 127 (45.2) | 1,958 | 278 |
| 82 | 17 | 8.408 | 6 | 133 [152.4] | 22,463 | 14,986 |

TABLE 12-continued

Ethylene Polymerization, Condition IX

| Ex. | Catalyst | Yield (g) | #Me/1000CH$_2$ | m.p. (° C.) ($\Delta H_f$) | Mn, $^1$HNMR | TON |
|---|---|---|---|---|---|---|
| 83 | 18 | 10.877 | 6 | 135 (158.1) | ≧9,594 | 19,387 |
| 84 | 19 | 0.102 | 11 | 131 (93.1) | 13,089 | 182 |
| 85 | 20 | 0.063 | 11 | 133 (69.0) | 3,850 | 112 |
| 86 | 21 | 7.101 | 11 | 131 (168.7) | 54,515 | 12,657 |
| 87 | 22 | 15.294 | 11 | 132 (190.5) | 3,965 | 27,260 |

TABLE 13

Ethylene polymerization (0.01 mmol catalyst, 10 mL TCB, 3.5 MPa ethylene, RT, 18 h)

| Ex. | Catalyst | Cocatalyst/amt | Yield (g) | #Me/1000CH$_2$ | m.p. (° C.) ($\Delta H_f$) | Mw/PDI | TON |
|---|---|---|---|---|---|---|---|
| 88 | 13 | B(C$_6$F$_5$)$_3$/10 eq | 11.829 | 34 | 115 (132.4) | 25,973/2.85[a] | 21,084 |
| 89 | 14 | B(C$_6$F$_5$)$_3$/10 eq | 15.198 | 36 | 115 (140.5) | 11,489/3.36 | 27,089 |
| 90 | 14 | BPh$_3$/10 eq | 14.994 | 23 | 114 (130.9) | 12,064/3.42 | 26,725 |
| 91 | 14 | none | 10.911 | 40 | 109 (99.0) | 11,590/2.82 | 19,448 |

[a] Bimodal, Mp 423.

TABLE 14

E/E-10-U Copolymerization, Condition X

| Ex. | Catalyst | Comonomer Mole % | Yield (g) | #Me/1000CH$_2$ | Mw | TON E/Comonomer |
|---|---|---|---|---|---|---|
| 92 | 1 | 1.9 | 9.168 | 16 | 43,604 | 227,278/4,514 |

EXAMPLES 93–127

In the following Examples the following ligands and π-allyl nickel complexes are made/used.

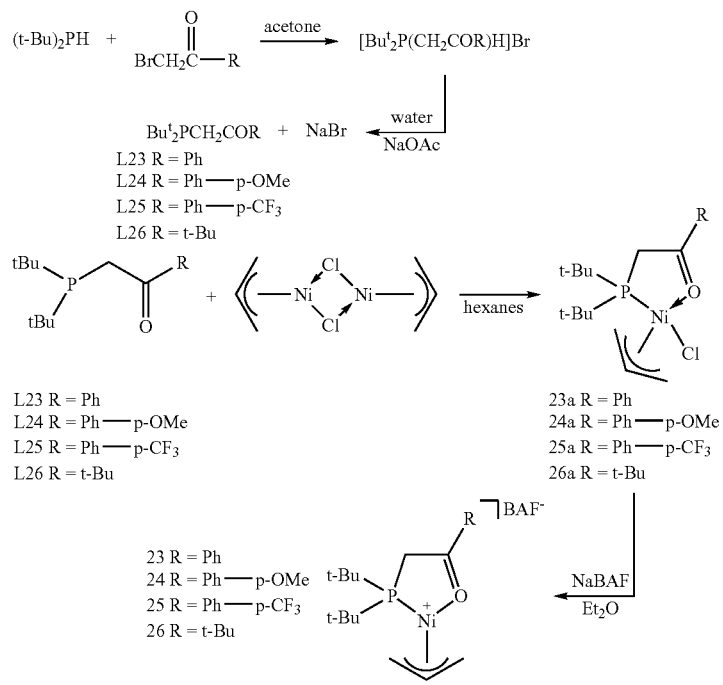

L23 R = Ph
L24 R = Ph—p-OMe
L25 R = Ph—p-CF$_3$
L26 R = t-Bu

23a R = Ph
24a R = Ph—p-OMe
25a R = Ph—p-CF$_3$
26a R = t-Bu

23 R = Ph
24 R = Ph—p-OMe
25 R = Ph—p-CF$_3$
26 R = t-Bu

For Examples 93–127 $^1$H and $^{31}$P NMR spectra were recorded on either a Varian 300 MHz or Bruker Avance-300 MHz spectrometers. $^1$H NMR spectra of polymer were taken in $C_6D_5Br$ at 120° C.

EXAMPLES 93–96

Syntheses of the β-Keto-Phosphine Ligands L23–L26.

The synthesis of these kinds of phosphines was described by B. L. Shaw, et al., *J. Chem. Soc. Dalton Trans.*, 1980, 299. A solution of 1 mL di-t-butyl-phosphine in 5 mL degassed acetone was added dropwise to the appropriate α-bromoketone in 15 mL degassed acetone with stirring. The mixture was stirred for a while and white crystals precipitated from the solution. The crystals were filtered and dried under vacuum then dissolved in 15 mL degassed water. A solution of sodium acetate (1.6 g, 20 mmol) in 10 mL degassed water was added to the phosphonium salt solution with stirring. The phosphine was extracted with diethyl ether and some colorless or light yellow oil was left after all the volatiles were removed under vacuum. For L25 and L26, the phosphonium salt didn't precipitate from the acetone solution. The acetone was removed under reduced pressure and the remaining solid was washed with pentane several times then dried. The results are summarized in Table 15.

TABLE 15

| Ex. | Ligand | R | Yield/% | Oil Color | $^{31}$P{$^1$H}/121 MHz/ CDCl$_3$/δ ppm |
|---|---|---|---|---|---|
| 93 | L23 | Ph | 55 | colorless | 31.17, s |
| 94 | L24 | Ph-p-OMe | 33 | colorless | 31.74, s |
| 95 | L25 | Ph-p-CF$_3$ | 76 | yellow | 31.40, s |
| 96 | L26 | t-Bu | 45 | colorless | 23.48, s |

EXAMPLES 97–100

Syntheses of the Ni (II) Chloride 23a–26a.

Nickel dimer, [Ni(C$_3$H$_5$)Cl]$_2$, was synthesized using a similar procedure to that described by G. Wilke et al., *Angew. Chem., Int. Ed. Engl.* 1966, 5, 151. A Schlenk flask was charged with [Ni(C$_3$H$_5$)Cl]$_2$ (108 mg, 0.4 mmol) and 15 mL dry, air-free hexane. The flask was cooled to −78° C. and a solution of appropriate phosphine in 10 mL hexane was added with stirring. The reaction mixture was allowed to warm to RT and stirred for 1~2 h. Solid product precipitated out. The solid was filtered and dried under vacuum. The results are summarized in Table 16.

TABLE 16

| Ex. | Pre-Cat. | Yield/% | Solid Color | $^1$H/300 MHz/ CD$_2$Cl$_2$ (central allyl H), δ/ppm | $^{31}$P{$^1$H}/121 MHz/ CD$_2$Cl$_2$, δ/ppm |
|---|---|---|---|---|---|
| 97 | 23a | 72 | yellow | 5.40, m | 50.32, s |
| 98 | 24a | 59 | yellow | 5.30, m | 49.85, s |
| 99 | 25a | 53 | yellow | 5.39, m | 53.67, s |
| 100 | 26a | 21 | orange | 5.13, m | 46.0, s |

EXAMPLES 101–104

Syntheses of the Ni (II) Catalysts 23–26.

A Schlenk flask was charged with the appropriate nickel chloride complex from Examples 97–100 and 20 mL dry, air-free diethyl ether. After the suspension was cooled to −78° C., a solution of NaBAF in 10 mL diethyl ether was added with stirring. The reaction mixture was allowed to warm to RT and stirred for 2~3 h. then filtered via cannula. The filtrate was concentrated under reduced pressure to about 5~10 mL and 50 mL pentane was added. Yellow solid precipitated from the solution and was filtered then dried under vacuum. Product can be recrystallized from pentane and dichloromethane. The results are summarized in Table 17.

TABLE 17

| Ex. | Catalyst | Yield/% | $^1$H/300 MHz/CD$_2$Cl$_2$ (central allyl H) δ/ppm | $^{31}$P{$^1$H}/121 MHz/ CD$_2$Cl$_2$ δ/ppm |
|---|---|---|---|---|
| 101 | 23 | 79 | 5.75, m | 73.50, s |
| 102 | 24 | 37 | 5.70, m | 73.25, s |
| 103 | 25 | 50 | 5.75, m | 74.50, s |
| 104 | 26 | 60 | 5.67, m | 71.71, s |

EXAMPLE 105

A Schlenk flask was charged with 50 mg of catalyst 23 which was dissolved in 5 mL CH$_2$Cl$_2$ under 101 kPa ethylene. The polymerization mixture was stirred for 22 h under 0 kPa ethylene then was quenched by addition of a few drops of acetone, 6 M HCl and excess methanol. Polyethylene precipitated from solution and was filtered out, washed with acetone and dried in vacuo at 70° C. overnight. The result is summarized in Table 18.

TABLE 18

| PE, g | TON | Mw |
|---|---|---|
| 0.2 | 170 | 10,400 |

EXAMPLES 106–110

Polymerizations were carried out in a 250 mL, mechanically stirred Parr® reactor equipped with an electric heating mantle controlled by a thermocouple in the reaction mixture. The reactor was heated under vacuum at 100° C. for 1 h before use. After the reactor was purged with ethylene for three times, 65 mL dry, air-free CH$_2$Cl$_2$ was added via syringe. Then the solvent was purged with ethylene at desired pressure for three times. Catalyst 23 was dissolved in 15 mL CH$_2$Cl$_2$ and was rapidly added to the reactor via cannula. The reaction mixture was stirred under the desired ethylene pressure then quenched by addition of acetone and methanol. The polymers were filtered from solution, washed with acetone and dried in vacuo at 70° C. overnight. The conditions and results are summarized in Table 19.

TABLE 19

| Ex. | Ni Cmpd mg | Solvent | Pressure MPa | T(Start) °C. | Exotherm °C. | Time H | PE g | TON | Mw |
|---|---|---|---|---|---|---|---|---|---|
| 106 | 50 | $CH_2Cl_2$ | 0.83 | RT | 52 | 22 | 15.0[d] | 13,000[a] | 9,400 |
| 107 | 20 | $CH_2Cl_2$ | 0.35 | RT | 35 | 22 | 6.86 | 15,000 | 12,700 |
| 108 | 20 | $CH_2Cl_2$ | 2.76 | RT | 129 | 3.25 | 25.9 | 57,000[a] | 2,600 |
| 109 | 20 | $CH_2Cl_2$/10% EtOAc[b] | 2.76 | RT | 30 | 3.25 | 0.1 | 220 | 7,100 |
| 110 | 20 | $CH_2Cl_2$/5% EtOAc[c] | 2.76 | 50[e] | 152 | 2.5 | 23.9 | 52,000[a] | 1,900 |

[a]PE filled up the reactor;
[b]dried by $MgSO_4$;
[c]dried by 4 Å molecular sieves;
[d]$T_m$ = 124.8° C.
[e]initiated by heating it up to 50° C.

EXAMPLES 111–115

Polymerizations were carried out in a 1000 mL, mechanically stirred Parr® reactor equipped with an electric heating mantle controlled by a thermocouple in the reaction mixture and a cooling system. The reactor was heated under vacuum at 100° C. for 1 h before use. After the reactor was purged with ethylene for three times, 185 mL dry, air-free toluene was added via syringe. Then the solvent was purged with ethylene at 2.76 MPa for three times and heated up to the desired temperature. Catalyst 23 was dissolved in 15 mL toluene and was rapidly added to the reactor via cannula. The reaction mixture was stirred under 2.76 MPa ethylene pressure, then quenched by addition of acetone and methanol. The polymers were filtered from the liquid, washed with acetone and dried in vacuo at 70° C. overnight. The conditions and results are summarized in Table 20.

TABLE 20

| Ex. | Ni Cmpd mg | T, °C. | Time h | PE g | TON | Mw |
|---|---|---|---|---|---|---|
| 111 | 2 | 60 (62)[a] | 3.25 | 0.6 | 13,200 | 7,500 |
| 112 | 5 | 60 (63) | 3.25 | 3.7 | 33,100 | 7,700 |
| 113 | 5 | 80 (85) | 3.25 | 6.7 | 60,200 | 7,300 |
| 114 | 5 | 100 (104) | 3.25 | 21.1[b] | 190,000 | 8,000 |
| 115 | 5 | 60 (62) | 9.75 | 4.9 | 43,300 | 7,700 |

[a]number in the parenthesis is the highest temperature that the reaction mixture reached.
[b]PE filled up the reactor.

EXAMPLES 116–125

Polymerizations were carried out in a 1000 mL, mechanically stirred Parr® reactor equipped with an electric heating mantle controlled by a thermocouple in the reaction mixture and a cooling system. The reactor was heated under vacuum at 100° C. for 1 h before use. After the reactor was purged with ethylene for three times, 185 mL dry, air-free toluene was added via syringe. Then the toluene was purged with ethylene at desired pressure for three times. The appropriate Ni[II] complex was dissolved in 15 mL toluene and was rapidly added to the reactor via cannula. The reaction mixture was heated up to the desired temperature and stirred under the desired ethylene pressure. The reaction was quenched by addition acetone and methanol. The polymers were filtered from the liquid, washed with acetone and dried in vacuo at 70° C. overnight. The conditions and results are summarized in Table 21.

TABLE 21

| Ex. | Catalyst | Ni Cmpd Mg | Pressure MPa | T, °C. | Time h | PE[d] g | TON | Mw |
|---|---|---|---|---|---|---|---|---|
| 116 | 23 | 10 | 2.76 | 60 (100)[a] | 3.25 | 51.9[b] | 230,000 | 6,100 |
| 117 | 23 | 5 | 2.76 | 60 (62) | 3.25 | 28.4[b] | 254,000 | — |
| 118 | 24 | 5 | 2.76 | 60 (62) | 3.25 | 55.6[b] | 500,000 | — |
| 119 | 23 | 5 | 2.76 | 40 (65) | 3.25 | 38.6[b] | 345,000 | — |
| 120 | 23 | 5 | 2.76 | 26 (88) | 3.25 | 85.4[b] | 763,000 | — |
| 121 | 23 | 5 | 2.76 | 26 (88) | 1 | 77.9[b] | 700,000 | — |
| 122 | 23 | 5 | 1.38 | 26 (46) | 1 | 27.6[b] | 250,000 | — |
| 123 | 23 | 5 | 0.69 | 26 (42) | 1 | 14.8 | 133,000 | — |
| 124 | 23 | 1 | 2.76 | 30 (36) | 1 | 25.5[b] | 1,138,000 | — |
| 125 | 23 | 1 | 2.76 | 30 | 0.25 | 1.67 | 75,000 | — |

[a]number in the parenthesis is the highest temperature that the reaction mixture ever reached
[b]PE filled up the reactor.

EXAMPLES 126–127

Polymerizations were carried out in a 1000 mL, mechanically stirred Parr® reactor equipped with an electric heating mantle controlled by a thermocouple in the reaction mixture and a cooling system. The reactor was heated under vacuum at 100° C. for 1 h before use. After the reactor was purged with ethylene for three times, dry, air-free toluene and 5.0 mL methyl-10-undecenoate were added via syringe. Then the solvent was purged with ethylene at desired pressure for three times. Catalyst 23 was dissolved in toluene and was rapidly added to the reactor via cannula. The reaction mixture was heated up to the desired temperature and stirred under desired ethylene pressure. The reaction was quenched by addition of acetone and methanol. The polymers were filtered from the liquid, washed with acetone and dried in vacuo at 70° C. overnight. The conditions and results are summarized in Table 22.

TABLE 22

| Ex. | Ni Cmpd mg | Toluene/ ml | Press. MPa | T ° C. | Time h | Polymer G | TON | Comonomer mol %[c] |
|---|---|---|---|---|---|---|---|---|
| 126 | 20 | 195 | 2.76 | 30 (105)[b] | 0.25 | 56.1 | 123,000 | 0.2 |
| 127 | 10 | 90 | 0.69 | 60 (61) | 4 | 3.9 | 17,000 | 1.0 |

[a]5 mL methyl-10-undecenoate, which was purified and dried before use.
[b]Reaction exothermed to 105° C. in 15 min.
[c]In product polymer, measured by high-tempreature $^1$H NMR.

EXAMPLE 128

Synthesis of Precatalyst 23a

To a suspension of [Ni(C$_3$H$_5$)Cl]$_2$ (0.300 g, 1.11 mmol) in 25 mL hexanes was added a solution of L23 (0.610 g, 2.31 mmol) in 10 mL hexanes. The resulting orange-yellow suspension was stirred at RT for 2 h. The reaction mixture was cooled to −78° C., and the bright orange solid was isolated by filtration, washed with hexanes (2×15 mL), and dried under high vacuum to yield 0.751 g (85%) of 23a. $^1$H NMR (200 MHz, CD$_2$Cl$_2$): δ 7.98 (d, 2H, $^3$J(HH) 8 Hz, Ar—Ho), δ 7.54 (m, 3H, Ar-Hm,p), δ 5.38 (m, 1H, allyl), δ 3.64 (d, 2H, $^3$J(PH) 10, —CH$_2$—), δ 3.45 (s(broad) 2H, allyl), δ 2.51 (s(broad), 2H, allyl), δ 1.43 (d, 18H, $^3$J(PH) 13, C—CH$_3$)

EXAMPLE 129

Synthesis of Catalyst 23

To a suspension of 23a (0.500 g, 1.25 mmol) in 25 mL diethyl ether at −78° C. was added a solution of NaBAF (1.106 g, 1.25 mmol) in 15 mL diethyl ether. The resulting yellow-orange solution was warmed to RT and stirred for 3 h. The yellow solution was separated from solid NaCl precipitate via filtration and the volume was reduced to ~5 mL. Fifty mL pentane was slowly added to precipitate a bright yellow solid. The product was isolated by filtration, washed with pentane (2×15 mL), and dried under high vacuum to yield 1.301 g (85%) of catalyst 23. $^1$H NMR (CDCl$_3$, 300 MHz): δ 7.97 (d, 2H, $^3$J(HH) 8.7 Hz, Ar—Ho), δ 7.74 (t,1H, $^3$J(HH) 9, Ar-Hp), δ 7.68 (s, 4H, BAF), δ 7.48 (t, 2H, $^3$J(HH) 9, Ar-Hm), δ 7.47 (s, 4H, BAF), δ 5.65 (m, 1H, allyl), δ 4.86 (d, 1H, $^3$J(HH) 7.5, allyl), δ 3.66 (d, 1H, $^3$J(HH) 14, allyl), δ 3.47 (dd, $^3$J(PH) 22, $^1$J(HH) 8, —CH$_2$—), δ 3.34 (m, 1H, allyl), δ 2.05 (d, 1H, $^3$J(HH) 13, allyl), δ 1.36 (d, 9H, $^3$J(PH) 15, C—CH$_3$), δ 1.19 (d, 9H, $^3$J(PH) 15, C—CH$_3$). $^{31}$P{$^1$H} NMR (CD$_2$Cl$_2$, 121 MHz): δ 73.1 (s). IR (CH$_2$Cl$_2$): ν 1610 cm$^{-1}$ (C=O stretch). Anal. (C$_{51}$H$_{42}$POBF$_{24}$Ni) calcd: C, 49.91; H, 3.45. Found: C, 50.04; H, 3.62.

EXAMPLES 130–146

General Procedure. 10 mg (8.2 μmol) of catalyst 23 was added to a flame-dried Schlenk flask under argon. The flask was back-filled twice with ethylene and placed in an oil bath at the appropriate reaction temperature. The flask was charged with 25 mL toluene and stirred under 101 kPa ethylene for the appropriate reaction time. The polymerization was quenched with 5 mL acetone and 1 mL HCl, and the mixture was poured into 250 mL stirring methanol to precipitate the polymer. The polymer was isolated by filtration, washed with acetone, and dried overnight in a vacuum oven. Results are given in Table 23. In Examples 130–133 the reaction produced a very small amount of polymer (visible upon precipitation into MeOH). However, the amount was so small that the polymer was not isolated and weighed. It is estimated that these reactions produce <2 mg polymer.

TABLE 23

| Ex. | Temp (° C.) | Time (h) | Yield (mg) | TON |
|---|---|---|---|---|
| 130 | 25 | 1 | <2 | — |
| 131 | 25 | 2 | <2 | — |
| 132 | 25 | 3 | <2 | — |
| 133 | 25 | 6 | <2 | — |
| 134 | 40 | 1 | 12 | 52 |
| 135 | 40 | 2 | 42 | 182 |
| 136 | 40 | 3 | 115 | 500 |
| 137 | 40 | 6 | 162 | 704 |
| 138 | 40 | 18 | 278 | 1208 |
| 139 | 60 | 1 | 11 | 48 |
| 140 | 60 | 2 | 28 | 122 |
| 141 | 60 | 3 | 131 | 570 |
| 142 | 60 | 6 | 180 | 783 |
| 143 | 80 | 1 | 5 | 22 |
| 144 | 80 | 2 | 65 | 282 |
| 145 | 80 | 3 | 105 | 456 |
| 146 | 80 | 6 | 118 | 513 |

EXAMPLES 147–153

Followed same polymerization procedure as in Examples 130–146, using 10 mg (8.2 μmol) of catalyst 23 plus 10.1 mg (10 μmol) H[OEt$_2$]$_2$BAF. Results are given in Table 24.

TABLE 24

| Ex. | Temp (° C.) | Time (h) | Yield (mg) | TON |
|---|---|---|---|---|
| 147 | 25 | 3 | 11 | 48 |
| 148 | 40 | 1 | <2 | — |
| 149 | 45 | 1 | 118 | 513 |
| 150 | 50 | 1 | 105 | 456 |
| 151 | 60 | 1 | 264 | 1148 |
| 152 | 70 | 1 | 154 | 670 |
| 153 | 80 | 1 | 462 | 2009 |

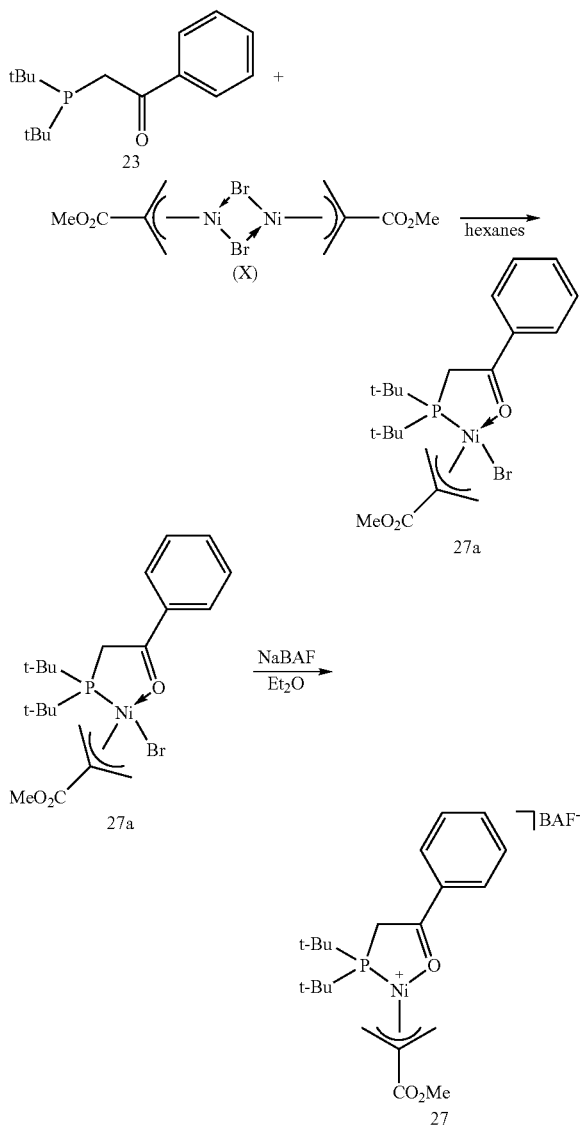

EXAMPLE 154

Synthesis of 27a (X) was prepared using the same literature procedure as nickel allyl chloride dimer, with the exception that methyl-2-bromomethyl acrylate was substituted for allyl chloride.

Complex 27a was prepared by following the same procedure as 23a using 0.400 g (0.841 mmol) (X) and 0.555 g (2.10 mmol) L23. Yields 0.629 g (75%) bright orange powder. $^1$H NMR (CD$_2$Cl$_2$, 200 MHz): δ 8.03 (d, 2H, Ar—H), δ 7.56 (m, 3H, Ar—H), δ 4.05 (s(broad), 2H, allyl), δ 3.83 (s, 3H, —OMe), δ 3.77 (d, 2H, —CH$_2$—), δ 1.42 (d, 18H, C—CH$_3$).

EXAMPLE 155

Synthesis of Catalyst 27

Catalyst 27 was prepared by following the same procedure as catalyst 23 using 0.300 g (0.589 mmol) 27a and 0.556 g (0.627 mmol) NaBAF. Yields 0.702 g (91%) bright yellow powder. $^1$H NMR (CD$_2$Cl$_2$, 300 MHz): δ 8.13 d, 2H, $^3$J(HH) 8.5 Hz, Ar—H), δ 7.88 (t, 1H, $^3$J(HH) 7.5, Ar—H), δ 7.72 (s, 8H, BAF), δ 7.62 (t, 2H, $^3$J(HH) 8, Ar—H), δ 7.55 (s, 4H, BAF), δ 5.37 (s(broad), 2H, allyl), δ 3.87 (s, 3H, —OMe), δ 3.62 (dd, 2H, $^3$J(PH) 14.7, $^1$J(HH) 7.8, —CH$_2$—), δ 2.25 (s(broad), 2H, allyl), δ 1.47 (d, 9H, $^3$J(PH) 16.5, C—CH$_3$), δ 1.27 (d, 9H, $^3$J(PH) 15, C—CH$_3$).

EXAMPLES 156–159

Followed same procedure as Examples 130–146, using 10.5 mg (8.2 μmol) of catalyst 27. Results are given in Table 25.

TABLE 25

| Ex. | Temp (° C.) | Time (h) | Yield (mg) | TON |
|---|---|---|---|---|
| 156 | 25 | 3 | <2 | — |
| 157 | 40 | 3 | 21 | 91 |
| 158 | 60 | 3 | 51 | 222 |
| 159 | 80 | 3 | 244 | 1060 |

EXAMPLES 160–167

Followed same procedure as Examples 130–146, using 10 mg (8.2 μmol) of catalyst 23, or 10.5 mg (8.2 μmol) of catalyst 27, plus 20.9 mg (40.8 μmol, 5 eq.) B(C$_6$F$_5$)$_3$. Results are given in Table 26.

TABLE 26

| Ex. | Catalyst | Temp (° C.) | Time (h) | Yield (mg) | TON |
|---|---|---|---|---|---|
| 1 | 23 | 25 | 1 | 57 | 248 |
| 2 | 27 | 25 | 1 | 130 | 568 |
| 3 | 23 | 40 | 1 | 20 | 87 |
| 4 | 27 | 40 | 1 | 194 | 843 |
| 5 | 23 | 60 | 1 | 51 | 221 |
| 6 | 27 | 60 | 1 | 278 | 1208 |
| 7 | 23 | 80 | 1 | 162 | 704 |
| 8 | 27 | 80 | 1 | 265 | 1152 |

EXAMPLES 168–177

Polymerization of 1-Hexene

General Procedure. Twenty mg (16.2 μmol) of catalyst 23, or 10.5 mg (10 μmol) of catalyst 27 plus 20.9 mg (40.8 μmol) B(C$_6$F$_5$)$_3$ (with 27 only) was added to a flame-dried Kontes® flask under argon. The flask was charged with 5 mL toluene and placed in an oil bath at the appropriate temperature. The flask was charged with 5 mL (39.98 mmol) 1-hexene, sealed, and stirred under static argon. The polymerization was quenched with 5 mL acetone, and the volatiles were removed via rotary evaporation. The residue was extracted with hexanes, which was subsequently passed through a plug of 2:1 silica gel/alumina. The solvent was removed from the extractions and the resulting clear, colorless oil was dried under high vacuum. Results are given in Table 27.

TABLE 27

| Ex. | Catalyst | Temp (° C.) | Time (h) | Yield (g) | TON |
|---|---|---|---|---|---|
| 168 | 23 | 25 | 16 | — | — |
| 169 | 23 | 80 | 3 | 0.078 | 52 |
| 170 | 23 | 80 | 16 | 1.640 | 1195 |
| 171 | 23 | 80 | 49 | 0.993 | 724 |
| 172 | 23 | 100 | 16 | 0.700 | 510 |
| 173 | 27 + B(C$_6$F$_5$)$_3$ | 25 | 18 | 0.043 | 62 |
| 174 | 27 + B(C$_6$F$_5$)$_3$ | 40 | 18 | 0.928 | 1345 |
| 175 | 27 + B(C$_6$F$_5$)$_3$ | 60 | 1 | 0.016 | 23 |
| 176 | 27 + B(C$_6$F$_5$)$_3$ | 60 | 3 | 0.744 | 1078 |
| 177 | 27 + B(C$_6$F$_5$)$_3$ | 60 | 18 | 1.243 | 1801 |

Polymers produced were typically thin, clear, colorless oils. A representative GPC result (Example 170): $M_w$=1400, $M_n$=1140.

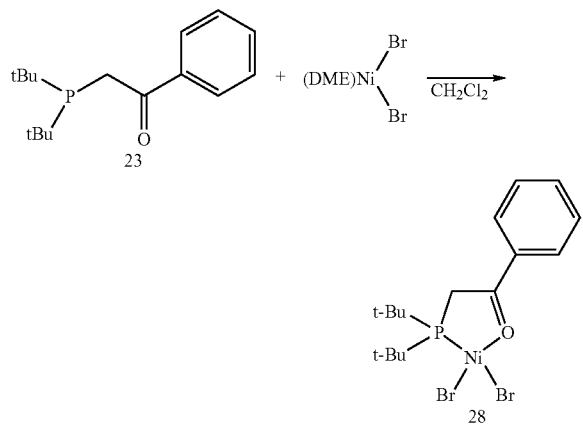

EXAMPLE 170

Synthesis of Catalyst 28

To a suspension of 0.500 g (1.62 mmol) (DME)NiBr$_2$ in 20 mL CH$_2$Cl$_2$ at RT was added a solution of 0.471 g (1.78 mmol) L23 in 5 mL CH$_2$Cl$_2$. The resulting dark brown/red suspension was stirred at room temperature for 16 h, during which time a light purple precipitate formed. The solid was isolated by filtration, washed with diethyl ether (2×15 mL), and dried under high vacuum to yield 0.493 g (63%) bright purple/pink powder.

EXAMPLES 179–184

General Procedure. Ten mg (20.7 μmol) of catalyst 28 was added to a flame-dried Schlenk flask under argon. The flask was back-filled twice with 101 kPa ethylene and charged with 50 mL toluene. The flask was then charged with 1.5 mL MMAO (6.42 wt. %, solution in heptane) and stirred under 101 kPa ethylene. The polymerization was quenched with 10 mL acetone/2 mL HCl and poured into stirring methanol to precipitate the polymer. The product was isolated by filtration, washed with acetone, and dried in a vacuum oven. Results are given in Table 28.

TABLE 28

| Ex. | Temp (° C.) | Time (min) | Yield (mg) | TON |
|---|---|---|---|---|
| 179 | 25 | 5 | 148 | 254 |
| 180 | 25 | 10 | 165 | 284 |
| 181 | 25 | 60 | 214 | 369 |
| 182 | 0 | 10 | 323 | 556 |
| 183 | 0 | 30 | 533 | 918 |
| 184 | 0 | 60 | 689 | 1187 |

EXAMPLES 185–191

General Procedure: In a drybox, a glass insert was loaded with the isolated Ni catalysts. TCB, and optionally comonomers, were added to the glass insert. A Lewis acid cocatalyst (typically BPh$_3$ or B(C$_6$F$_5$)$_3$) was often added to the solution. The insert was then capped and sealed. Outside of the drybox, the tube was placed under ethylene and was shaken mechanically for about 18 h. The resulting reaction mixture was mixed with methanol, filtered, repeatedly washed with methanol and the solid polymer dried in vacuo. Results are given in Tables 29 and 30.

TABLE 29

Ethylene/Polar Monomer Copolymerization Using 0.02 mmole 1, with or without B(C$_6$F$_5$)$_3$, with a Total Volume of 10 mL of TCB and Polar Monomer, at 80° C. under 3.4 MPa of E

| Ex | B(C$_6$F$_5$)$_3$ | Polar Monomer | Polar Monomer Volume (mL) | Yield (g) |
|---|---|---|---|---|
| 185 | 40 eq | CH$_2$=CHCH$_2$C(CH$_3$)$_2$CH$_2$OH | 2 | 1.617 |
| 186 | 0 eq | CH$_2$=CHCH$_2$C(CH$_3$)$_2$CH(O)CH$_2$ (epoxide) | 3 | 3.124 |
| 187 | 40 eq | CH$_2$=CH(CH$_2$)$_2$C(O)CH$_3$ | 3 | 0.030 |
| 188 | 40 eq | CH$_2$=CHCH$_2$CH(CO$_2$Et)$_2$ | 3 | 0.558 |
| 189 | 40 eq | CH$_2$=CH(CH$_2$)$_7$C(CH$_2$O)$_3$CCH$_3$ | 3 | 7.699 |

TABLE 30

Ethylene/CO Copolymerization Using 0.02 mmole Catalyst, 40 eq B(C$_6$F$_5$)$_3$, 10 mL TCB, at 100° C. under 2.8 MPa Ethylene/CO (9:1 ratio) for 16 h in Shaker Tubes

| Ex | Catalyst | Yield (g) |
|---|---|---|
| 190 | 11 | 0.027 |
| 191 | 14 | 0.528 |

EXAMPLES 192

In a drybox, a glass insert was loaded with 0.0025 mmole 1, 6 mL TCB and 4 mL E-10-U. The insert was then capped and sealed. Outside of the drybox, the tube was placed under 6.9 MPa ethylene and was shaken mechanically at 100° C. for 18 h. The resulting reaction mixture was mixed with methanol, filtered, repeatedly washed with methanol and the solid polymer dried in vacuo. White solid (0.863 g) was obtained.

$^1$HMNR: 6.9 mole % E-10-U. 30Me/1000CH$_2$. GPC (TCB, 135° C.): Mw=10,625; Mn=4,667; PDI=2.3. The polymer had a melting point of 119° C. (147.4 J/g) based on DSC.

EXAMPLES 193–203

General Information Regarding Molecular Weight Analysis

GPC molecular weights are reported versus polystyrene standards. Unless noted otherwise, GPC's were run with RI detection at a flow rate of 1 mL/min at 135° C. with a run time of 30 min. Two columns were used: AT-806MS and WA/P/N 34200. A Waters RI detector was used and the solvent was TCB with 5 grams of BHT per gallon. Dual UV/RI detection GPC was run in THF at rt using a Waters 2690 separation module with a Waters 2410 RI detector and a Waters 2487 dual absorbance detector. Two Shodex columns, KF-806M, were used along with one guard column, KF-G. In addition to GPC, molecular weight information was at times determined by $^1$H NMR spectroscopy (olefin end group analysis) and by melt index measurements (g/10 min at 190° C.).

General Procedure A for Ethylene Polymerizations and Copolymerizations:

In a nitrogen-filled drybox, a 40 mL glass insert was loaded with the nickel compound and, optionally, a Lewis acid (e.g., BPh$_3$ or B(C$_6$F$_5$)$_3$) and borate (e.g., NaBAF or LiBArF) and any other specified cocatalysts. Next, the solvent was added to the glass insert followed by the addition of any co-solvents and then comonomers. The insert was greased and capped. The glass insert was then loaded in a pressure tube inside the drybox. The pressure tube was then sealed, brought outside of the drybox, connected to the pressure reactor, placed under the desired ethylene pressure and shaken mechanically. After the stated reaction time, the ethylene pressure was released and the glass insert was removed from the pressure tube. The polymer was precipitated by the addition of MeOH (~20 mL). The polymer was then collected on a frit and rinsed with MeOH and, optionally, acetone. The polymer was transferred to a pre-weighed vial and dried under vacuum overnight. The polymer yield and characterization were then obtained.

Nickel compounds used in these examples are shown below.

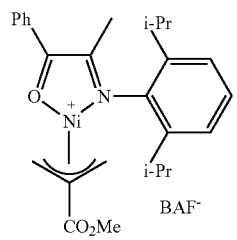
F-1

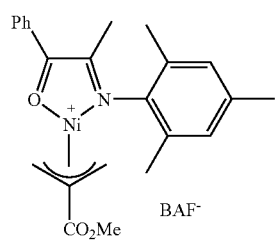
F-2

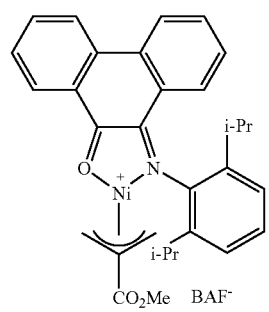
F-3

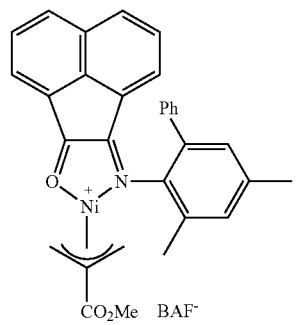
F-4

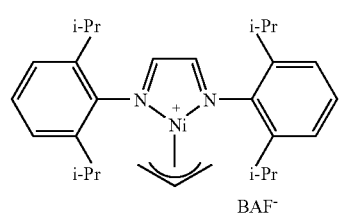
F-5

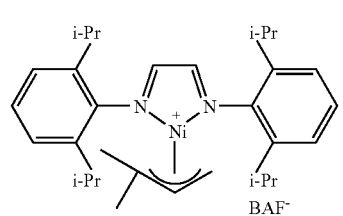
F-6

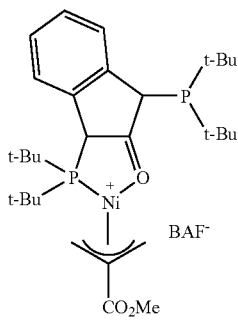

F-7

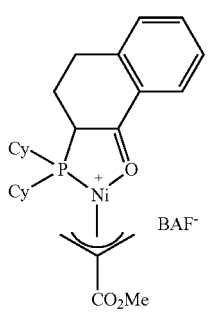

F-8

Ligand and Catalyst Syntheses

The imine-ketone and alpha-diimine ligands and their Ni complexes F-1 through F-6 were synthesized according to standard literature methods (tom Dieck, h.; Svoboda, M.; Grieser, T., Z. Naturforsch, 1981, 36b, 832). Typically a small excess of aniline was added to the diketone in methanol together with a catalytic amount of formic acid. The reaction mixtures were stirred for several days and the precipitate was collected on a frit, washed with methanol, and dried in vacuo.

The ligand for complex F-7 was synthesized as follows: In a nitrogen-filled drybox, 2-indanone (0.50 g, 3.78 mmol) was placed in a round-bottom flask and dissolved in 20 mL of THF. Sodium hydride (0.77 g, 30.3 mmol) was added to the flask and the reaction mixture was stirred for approximately 1 h. Next, (t-Bu)$_2$PCl (1.37 g, 7.57 mmol) was added to the reaction mixture and stirring was continued overnight. The solution was filtered through a frit with Celite®. The solid was dissolved in pentane and filtered again to yield 1.59 g of a yellow powder. $^1$H NMR (CD$_2$Cl$_2$, diagnostic resonances) δ 1.3–1.0 ppm (two major sets of doublets, P(t-Bu)).

The ligand for complex F-8 was synthesized as follows: In a nitrogen-filled drybox, tetralone (2.92 g, 20 mmol) was added dropwise to a solution of LDA (2.14 g, 20 mmol) in Et$_2$O (25 mL). The tetralone enolate was isolated by precipitation with anhydrous hexane followed by filtration and drying. Next, Cy$_2$PCl (0.232 g, 1.0 mmol) and tetralone enolate (0.152 g, 1.0 mmol) were each dissolved in THF (1 mL), mixed, and the reaction mixture was stirred overnight. The solvent was removed in vacuo. The compound was dissolved in toluene, the solution was filtered, and the toluene was removed to give the product. $^{31}$P NMR (C$_6$D$_6$): δ 135.16; IR shows very intense band at 1716 cm$^{-1}$.

The Ni complexes F-1 through F-8 were synthesized by stirring an Et$_2$O solution of the ligand (1 equiv), the appropriately substituted [(allyl)Ni(halide)]$_2$ precursor (0.5 equiv) and NaBAF (1 equiv) in a nitrogen-filled drybox for several hours. The solution was then filtered through a frit with dry Celite® and the solvent was removed in vacuo. The product was washed with pentane and then dried in vacuo.

Results for Examples 193–203 are listed in Tables 31 and 32 below. The polymerizations were carried out according to the General Polymerization Procedure A. Varying amounts of acrylate homopolymer are present in some of the isolated polymers. In Tables 31 and 32, the yield of the polymer is reported in grams and includes the yield of the dominant ethylene/acrylate copolymer as well as the yield of any acrylate homopolymer that was formed. Molecular weights were determined by GPC, unless indicated otherwise. Mole percent acrylate incorporation and total Me were determined by $^1$H NMR spectroscopy, unless indicated otherwise. Mole percent acrylate incorporation is typically predominantly IC, unless indicated otherwise.

TABLE 31

Ethylene/Acrylate Copolymerizations (0.02 mmol Ni Cmpd, 1 mL EGPEA, 9 mL Solvent, 20 equiv B(C$_6$F$_5$)$_3$, 10 equiv NaBAF, 6.9 MPa E, 18 h)

| Ex. | Cmpd | Solvent | Temp °C. | Yield g | Acrylate Incorp. mol % | M.W. | Total Me |
|---|---|---|---|---|---|---|---|
| 193 | F-1 | TCB | 110 | 0.316 | 0.8 | M$_p$ = 2,201; M$_w$ = 42,507; M$_n$ = 1,561; PDI = 27.23 | 31.6 |
| 194 | F-7 | p-Xylene | 120 | 1.04 | 1.0 0.43 IC 0.54 EG | M$_p$ = 988; M$_w$ = 1,719; M$_n$ = 780; PDI = 2.20 | 22.7 |
| 195 | F-8 | p-Xylene | 120 | 0.053 | 2.0 1.57 IC 0.47 EG | M$_n$($^1$H) = 2,218.8 | 32.4 |
| 196 | F-2 | TCB | 110 | 0.076 | a | Nd | Nd |
| 197 | F-3 | TCB | 100 | 0.142 | a | M$_p$ = 19,594; M$_w$ = 19,765; M$_n$ = 3,835; PDI = 5.15 | Nd |

TABLE 31-continued

Ethylene/Acrylate Copolymerizations (0.02 mmol Ni Cmpd, 1 mL EGPEA, 9 mL Solvent, 20 equiv B(C$_6$F$_5$)$_3$, 10 equiv NaBAF, 6.9 MPa E, 18 h)

| Ex. | Cmpd | Solvent | Temp ° C. | Yield g | Acrylate Incorp. mol % | M.W. | Total Me |
|---|---|---|---|---|---|---|---|
| 198 | F-4 | TCB | 120 | 0.547 | a | $M_p$ = 3,778; $M_w$ = 5,551; $M_n$ = 2,043; PDI = 2.72 | Nd | a Copolymer resonances are observable in the $^1$H NMR spectrum, but were not integrated due to overlap with significant homopolymer resonances.

TABLE 32

Ethylene Homopolymerization and Ethylene/Acrylate Copolymerization, 6.9 MPa E (18 h)

| Ex. | Cmpd (mmol) | Acrylate mL (Solvent mL) | LA equiv | Temp ° C. | Yield g | Incorp. mol % | M.W. | Total Me |
|---|---|---|---|---|---|---|---|---|
| 199 | F-5$^a$ (0.06) | None (CDCl$_3$, 5) | None | 80 | 20.55 | — | Nd | Nd |
| 200 | F-3 (0.06) | None (CDCl$_3$, 5) | None | 80 | 0.974 | — | Nd | Nd |
| 201 | F-3 (0.06) | None (C$_6$D$_6$, 5) | None | 25 | 3.60 | — | Nd | Nd |
| 202 | F-6 (0.02) | THA 2 (TCB 8) | None | 120 | 0.63 | 0.64 ($^{13}$C) | Dual UV/RI. UV: $M_p$ = 8,098; RI: $M_p$ = 9,383; | 34.0 |
| 203 | F-6 (0.02) | THA 2 (TCB 8) | B(C$_6$F$_5$)$_3$ 40 | 120 | 2.37 | 0.23 ($^{13}$C) | $M_p$ = 12,775; $M_w$ = 13,777; $M_n$ = 7,165; PDI = 1.92 | 43.1 ($^{13}$C) | a Complex F-5 yields higher productivity for ethylene homopolymerization in the absence of a Lewis acid than a number of other alpha diimine nickel allyl complexes. For some comparative examples that were run in the same reactor as the present example and which exhibited lower productivity in the absence of Lewis acid cocatalyst, see U.S. Pat. No. 5,886,224 examples 521–531 (no Lewis acid present) and examples 532–537 (Lewis acid present).

EXAMPLES 204–205

A 600 mL Parr® reactor was cleaned, heated up under vacuum, and then allowed to cool under nitrogen. In a drybox, 10.0 mg of 3 (and also 20 mg BPh$_3$ for Example 205) was dissolved in 60 mL chlorobenzene in a 150 mL addition cylinder. The cylinder was brought out of the drybox and was attached to the Parr® reactor. The solution in the addition cylinder was pressured into the 80° C. reactor under 2.1 MPa. Nitrogen was quickly vented. Ethylene pressure (~6.9 MPa) was applied. The autoclave was allowed to stir (600 RPM) at 100° C. under 6.9 MPa of ethylene for 1 h. The heating source was removed and ethylene was vented. The autoclave was back-filled with 700 kPa nitrogen and the nitrogen was vented after brief stirring. This was repeated two more times. The room temperature mixture was poured into 500 mL methanol, filtered, and washed with methanol. The resulting polymer was blended with methanol, filtered, and washed with methanol. Repeated this blending/washing procedure two more times. It was dried in vacuo overnight. Results are shown in Table 33.

TABLE 33

| Ex. | Equiv. Lewis Acid | Yield (g) | Mw/PDI |
|---|---|---|---|
| 204 | None | 18.31 | 10,819/2.6 |
| 205 | 10 eq BPh$_3$ | 20.83 | 10,673/2.9 |

EXAMPLES 206–208

A 600 mL Parr® reactor was cleaned, heated under vacuum, and then allowed to cool under nitrogen. In the drybox, 12.4 mg of 14 (and also 182 mg BPh$_3$ for Example 207, or 385 mg B(C$_6$F$_5$)$_3$ for Example 208) was dissolved in 90 mL toluene and 60 mL E-10-U in a 300 mL RB flask. It was sealed using a rubber septum. Outside the drybox, a 100° C. oil bath was prepared. The RB flask was removed from the drybox. The solution was transferred via cannula into the autoclave under positive nitrogen pressure. The autoclave was sealed and pressurized to 700 kPa nitrogen. Nitrogen was then vented. The pressuring/venting was repeated two more times. At about 35 kPa nitrogen, the autoclave was stirred at about 600 rpm. Ethylene pressure (~4.5 MPa) was applied. The autoclave was quickly placed in the preheated 100° C. bath. The pressure of the autoclave was adjusted to about 5.5 MPa and the temperature of the bath was adjusted to make the reaction temperature about 100° C. It was stirred at this temperature and pressure for 2 hr. The heating source was removed and ethylene was vented. The autoclave was back-filled with 700 kPa nitrogen and the nitrogen was vented after brief stirring. This was repeated two more times. The room temperature mixture was poured into 500 mL methanol, filtered, and washed with methanol. The resulting polymer was blended with methanol, filtered, and washed with methanol. This procedure was repeated two more times. It was dried in vacuo overnight. Results are shown in Table 34.

TABLE 34

| Ex. | Equiv. Lewis Acid | Yield (g) | E-10-U (Mole %) | #Me/ 1000CH$_2$ |
|---|---|---|---|---|
| 206 | none | 29.57 | 1.3 | 6 |
| 207 | 80 BPh$_3$ | 44.07 | 1.6 | 6 |
| 208 | 80 eq B(C$_6$F$_5$)$_3$ | 25.30 | 2.3 | 6 |

EXAMPLE 209

Ligand G-1

The syntheses of ligand G-1 was published in WO 00/50470.

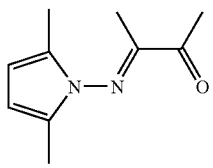

G-1

Ligand G-2—Acenaphthenedionemono[2,5-diisopropylpyrrol-1-imine]

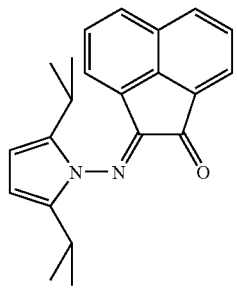

G-2

A 100 mL round bottom flask was charged with 0.3215 g (1.76 mmol) of acenaphthenequinone, 0.586 g (3.53 mmol) of 1-amino-2,5-diisopropylpyrrole, 50 mL methanol and 1 drop of formic acid. The reaction was monitored by TLC with elute of 30% ethyl acetate in hexane and stirred 7 days at RT. The solvent was removed under vacuum and the unreacted pyrrole was recovered by sublimation. The red residue was extracted with hexane. 0.40 g (1.2 mmol) of orange red powder was obtained in 69% yield. $^1$H NMR (CDCl$_3$): δ 8.12 (d-d, 2, H-acen), 8.01 (d, 1, H-acen), 7.77 (t, 1, H-acen), 7.50 (t, 1, H-acen), 6.70 (d, 1, H-acen), 5.98 (s, 2, H-py), 2.60 (m, 2, H—Pr-i), 1.10 (d, 6, CH$_3$—Pr-i), 0.94 (d, 6, CH$_3$—Pr-i).

Copolymerization of Ethylene and Polar-Comonomers

Into a glass vial used for shaker reaction, were weighed 0.02 mmol of Ligand G-1 or G-2, 1 equivalent of allyl-Ni dimer ([(2-MeO$_2$C—C$_3$H$_4$)NiBr]$_2$) and 10 equivalent of NaBaf. 2 mL of ether was added into the vial and shaken well. After two hours during which time the most of the ether was evaporated off, 20 equivalent of tris(pentafluorophenyl) borane cocatalyst, 9 mL of 1,2,4-trichlorobenzene and 1 mL of ethylene glycol phenyl ether acrylate was added into the vial. The vials were placed into a shaker tube, sealed and taken out from the dry box. The shaker tube was connected to a high pressure, ethylene shaker reaction unit. Reaction conditions for polymerization were: 1000 psi ethylene, 120° C., 18 hours. The results are presented below in Table 35.

TABLE 35

| Lig | Polym yield (g) | Catalyst Product (Kg/g) | M$_w$ | M$_n$ | M$_n$/M$_w$ | Me/ 1000 CH$_2$ | Comon. Incorp. (Mol %) | Peak MP (° C.) ΔH (J/g) |
|---|---|---|---|---|---|---|---|---|
| G-1 | 0.5487 | 0.44 | 4870 | 1537 | 3.17 | — | — | 119 shoulder |
| G-2 | 1.5404 | 1.26 | Bimodal | | | 36.0 | 0.13 | 86 104 |
| G-2 | 1.3004 | 1.11 | 24477 | 627 | 39.05[b] | — | Trace | 98 120 |
| G-2 | 0.8664 | 0.72 | 7109 | 1599 | 4.45[b] | | | 86 broad |
| G-2 | 1.0002 | 0.85 | 64795 | 1340 | 48.35 | | | |

Notes:
a. 20 equivalent of NaBArf,
b. RI data for GPC in THF, dual detector RI-UV,
c. [AlMe$_2$(Et$_2$O)]$^+$[MeB(C$_6$F$_5$)$_3$]$^-$ cocatalyst and p-xylene solvent,
d. Hexyl acrylate comonomer.

EXAMPLE 210

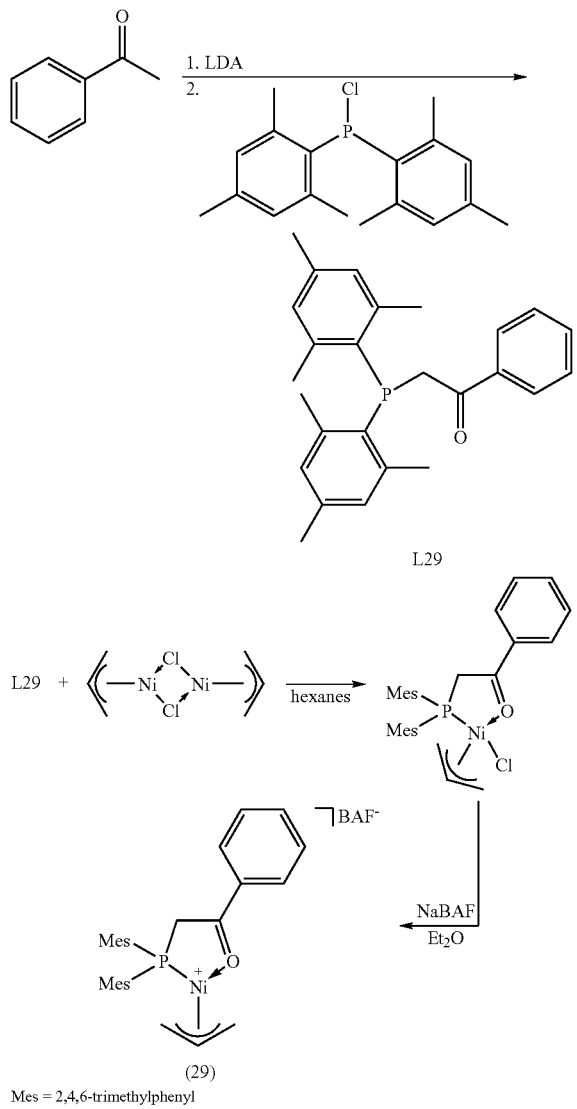

Mes = 2,4,6-trimethylphenyl

Synthesis of L29. Acetophenone (0.383 mL, 3.28 mmol) and 8 mL THF were added to a flame-dried Schlenk under argon. The solution was cooled to −78° C. and charged with 3.28 mmol LDA (solution in 8 mL THF). The reaction mixture was warmed to RT and stirred for 1.5 h, during which time a pale yellow solution formed. This was added via cannula to a pre-cooled (−78° C.) solution of 1.00 g (3.28 mmol) dimesitylchlorophosphine in 8 mL THF. The resulting yellow/orange solution was warmed to RT and stirred for 2 h. The solvent was removed in vacuo and the residue was extracted with 30 mL hexanes and passed through a plug of silica gel. The extract solvent was removed in vacuo to yield a pale yellow amorphous solid. Pentane (20 mL) was added with vigorous stirring to yield a white powder. The product was isolated via filtration, washed with 10 mL pentane, and dried in vacuo to yield 0.158 g (12%) L29. $^1$H NMR (300 MHz, CD$_2$Cl$_2$). δ 7.81 (d, 2H, aryl H$_o$), 7.51 (t,1H, aryl H$_p$), 7.37 (m, 2H, aryl H$_m$), 6.73 (d, 4H, Mes H$_m$), 4.15 (d, 2H, —CH$_2$—), 2.20 (s, 6H, Mes-Me$_p$), 2.16 (s, 12H, Mes-Me$_o$). $^{31}$P{$^1$H} NMR (121 MHz, CD$_2$Cl$_2$). δ −25.7.

Synthesis of 29. A solution of 75 mg (0.193 mmol) L29 in 8 mL Et$_2$O was added via cannula to a solution of 25.5 mg (0.094 mmol) Ni-allyl dimer in 5 mL Et$_2$O. The resulting orange-yellow solution was stirred at RT for 3 h. The solvent was removed in vacuo to yield a orange/yellow microcrystalline solid. The product was dried in vacuo to yield 52 mg (53%) of a solid. $^1$H NMR (400 MHz, CD$_2$Cl$_2$). δ 7.68 (broad s, 2H, aryl H$_o$), 7.35 (broad s, 1H, aryl H$_p$), 7.32 (broad s, 2H, aryl H$_m$), 6.84 (s, 4H, Mes H$_m$), 5.40 (broad s, 1H, allyl), 4.43 (broad s, 2H, allyl), 3.43 (broad s, 2H, allyl), 2.46 (s, 6H, Mes-Me$_p$), 2.20 (s, 12H, Mes-Me$_o$). $^{31}$P{$^1$H} NMR (161.8 MHz, CD$_2$Cl$_2$). δ −0.66. This solid (50 mg, 0.095 mmol), NaBAF (84 mg, 0.095 mmol), and 10 mL Et$_2$O were added to a flame-dried Schlenk flask at −78° C. The reaction was warmed to room temperature and stirred for 1.5 h. The pale yellow solution was isolated via cannula filtration and the solvent removed to yield a yellow oil. Pentane (20 mL) was added with vigorous stirring to yield a yellow powder. The product was isolated via filtration, washed with 10 mL pentane, and dried in vacuo to yield 86 mg (67%) 29. $^1$H NMR (400 MHz, CD$_2$Cl$_2$). δ 8.02 (d, 2H, aryl H$_o$), 7.83 (t, 1H, aryl H$_p$), 7.72 (s, 8H, BAF), 7.57 (m, 2H, aryl H$_m$), 7.55 (s, 4H, BAF), 6.98 (d, 4H, Mes H$_m$), 5.87 (m,1H, allyl), 4.84 (broad s, 1H, allyl), 3.70 (d, 1H, allyl), 3.06 (s, 1H, allyl), 2.42 (s, 12H, Mes-Me$_o$), 2.29 (s, 6H, Mes-Me$_p$), 1.97 (d, 1H, allyl). $^{31}$P{$^1$H} NMR (161.8 MHz, CD$_2$Cl$_2$). δ 4.83.

EXAMPLES 211–216

Polymerization of Ethylene (1 atm., 0 Pa gauge) with 29. Followed same procedure as Examples 130–146 using 2.0 mg (1.48 μmol) 3. Results are listed in Table 36.

TABLE 36

| Ex. | Temp (° C.) | Time (h) | Yield (g) | TON |
| --- | --- | --- | --- | --- |
| 211 | 25 | 1 | 2.170 | 52490 |
| 212 | 25 | 3 | 4.141 | 99750 |
| 213 | 40 | 1 | 1.797 | 43290 |
| 214 | 40 | 3 | 4.835 | 116470 |
| 215 | 60 | 1 | 1.633 | 39340 |
| 216[a] | 60 | 3 | 1.868 | 25990 |

[a]$M_n$ = 1090, 5 branches/1000 carbons (determined by $^1$H NMR)

EXAMPLE 217

Polymerization of Ethylene (1.38 MPa) with 29. Followed same procedure as Examples 111–115 using 2.0 mg (1.48 μmol) 3. Results are listed in Table 37.

TABLE 37

| Ex. | Temp (° C.) | Time (h) | Yield (g) | TON |
| --- | --- | --- | --- | --- |
| 217 | 25 | 1 | 28.170 | 678570 |

EXAMPLE 218

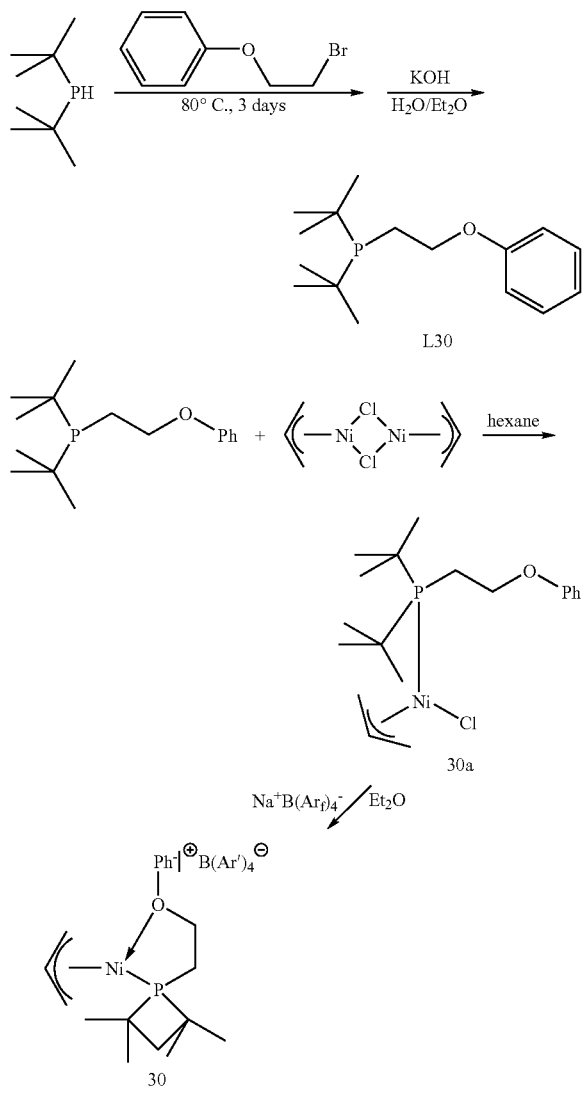

Synthesis of (19a). L19, t-Bu₂PCH₂CH₂OPh, was synthesized using a procedure described by h. Werner et al., *Organometallics* 2000, 19, 4756. A Schlenk flask was charged with [Ni(C₃H₅)Cl]₂ (54 mg, 0.2 mmol) and 15 mL dry, air-free hexane. The flask was cooled to −78° C. and a solution of L19 (103 mg, 0.4 mmol) in 10 mL hexane was added with stirring. The reaction mixture was allowed to warm to RT and stirred for 1.5 h. Product precipitated out as yellow solid. The solid was filtered and dried under vacuum to give 88 mg (56%) of 19a. ¹H NMR (CD₂Cl₂, 300 M): δ 6.85–7.2 ppm (total 5H, Ar—H); 5.25 (m, 1 H, central allyl H); 4.21 (broad, 2H); 3.95 (broad, 1H); 3.1 (broad, 1H); 2.9 (broad, 1H); 2.2 (broad, 2H); 1.6 (broad, 1H); 1.25 (d, 18H, t-Bu H). ³¹P NMR (CD₂Cl₂, 121 M): δ 48.78 ppm.

Synthesis of 19. A Schlenk flask was charged with the nickel chloride 19a (80 mg, 0.2 mmol) and 20 mL dry, air-free diethyl ether. After the yellow suspension was cooled to −78° C., a solution of NaBAF (178 mg, 0.2 mmol) in 10 mL diethyl ether was added with stirring. The reaction mixture was allowed to warm to RT and stirred for 1.5 h, then filtered via cannula. 10 mL hexane was added to the filtrate. Removal of solvents afforded 0.20 g (81%) of 19 as yellow solid. ¹H NMR (CD₂Cl₂, 300 M): δ 7.5–7.8 ppm (total 12 H, BAF-H); 7.1 to 7.5 (total 5H, Ar—H); 5.5 (m,1H, central allyl H); 4.4 (m, 1H); 4.2 (m, 1H); 3.3 (broad, 2H); 3.0 (d of d, 1H); 2.05 (m, 1H); 1.9 (broad doublet, 2H); 1.3 (d of d, 18H, t-Bu H). ³¹P NMR (CD₂Cl₂, 121 M): δ 72.35 ppm.

EXAMPLE 219

Polymerization was carried out in a 1000 mL, mechanically stirred Parr® reactor equipped with an electric heating mantle controlled by a thermocouple in the reaction mixture and a cooling system. The reactor was heated under vacuum at 100° C. for 1 h before use. After the reactor was purged with ethylene three times, 185 mL dry, air-free toluene was added via syringe. The solvent was then purged with ethylene at 2.76 MPa three times. 19 (5 mg, 4.1 μmol) was dissolved in 15 mL toluene and was rapidly added to the reactor via cannula. The reaction mixture was heated to 60° C. and stirred under 2.76 MPa ethylene for 1 h. The reaction was quenched by addition of acetone and methanol. Removal of solvents afforded 4.23 g colorless oil. TON≈37,000. Mn≈190 (determined by ¹H NMR), 80% linear α-olefins and 20% vinylidenes.

EXAMPLES 220–221

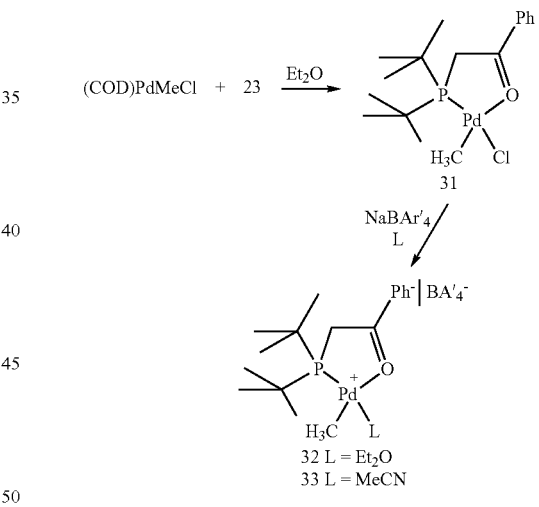

32 L = Et₂O
33 L = MeCN

Synthesis of 31: 23 (0.441 g, 1.67 mmol) was dissolved in 10 mL diethyl ether and added via cannula to a solution of (COD)PdMe(Cl) (0.400 g, 1.51 mmol) in 25 mL diethyl ether. The resulting white-yellow suspension was stirred at room temperature for 6 hours. The white powder product was isolated by filtration, washed with diethyl ether (2×10 mL), and dried in vacuo to yield 31 (0.513 g, 81% yield). ¹H NMR (300 MHz, CD₂Cl₂): δ 8.06 (d, 2H, J=1.8 Hz, Ar—H₀), 7.74 (t, 1H, J=7.5 Hz, Ar—H$_p$), 7.55 (m, 2H, Ar—H$_m$), 3.58 (d, 2H, ²J$_{HP}$=9.3 Hz, —CH₂—), 1.37 (d, 18H, ³J$_{HP}$=14.4 Hz, —C(CH₃)₃), 1.03 (d, 3H, ³J$_{HP}$=2.1 Hz, Pd—CH₃). ¹³C{¹H} NMR (75.5 MHz, CD₂Cl₂): δ 206.0 (d, ²J$_{CP}$=3.1 Hz, C=O), 136.0 (Ar—C$_p$), 134.5 (d, ³J$_{CP}$=3.9 Hz, Ar—C$_{ipso}$), 130.5 (Ar—C₀), 129.5 (Ar—C$_m$), 37.2 (d, J$_{CP}$=20.0 Hz, —CH₂—), 35.7 (d, J$_{CP}$=16.8 Hz, —C(CH₃)₃), 29.2 (d, ²J$_{CP}$=4.7 Hz, —C(CH₃)₃), −11.6 (d, ²J$_{CP}$=2.0 Hz, Pd—CH$_3$). $^{31}$P{$^1$H} NMR (162 MHz, CD$_2$Cl$_2$): δ 70.5. IR (CH$_2$Cl$_2$): ν (C=O)=1626 cm$^{-1}$. Anal Calcd for C$_{17}$H$_{28}$ClOPPd: C, 48.47; H, 6.70. Found: C, 48.99; H, 6.98.

EXAMPLE 220

Synthesis of 32: 31 (0.100 g, 0.237 mmol) and NaBAr'$_4$ (0.220 g, 0.243 mmol) was added to a Schlenk flask and cooled to −78° C. Diethyl ether (15 mL) was added and the resulting pale-yellow solution was slowly warmed to 0° C. and stirred for 3 h. The yellow solution was separated from the gray solid NaCl precipitate via cannula filtration, and the solvent was removed in vacuo to yield a white-yellow oily residue. Pentane (15 mL) was added and the mixture was vigorously stirred at 0° C. for 1 h, during which time a white-gray solid precipitated from the clear, colorless solution. The product was isolated by filtration, washed with pentane (2×10 mL), and dried in vacuo to yield 32 (0.223 g, 71% yield). The product was recrystallized from diethyl ether/pentane. $^1$H NMR (300 MHz, CD$_2$Cl$_2$): δ 8.03 (d, 2H, J=7.6 Hz, Ar—H$_o$), 7.81 (t, 1H, J=7.5 Hz, Ar—H$_p$), 7.58 (m, 2H, Ar—H$_m$), 3.81 (q, 4H, J=7.0 Hz, —O(CH$_2$CH$_3$)$_2$), 3.71 (d, 2H, $^2$J$_{HP}$=9.6 Hz, —CH$_2$—), 1.50 (t, 6H, J=7.0 Hz, —O(CH$_2$CH$_3$)$_2$), 1.39 (d, 18 H, $^3$J$_{HP}$=15.6 Hz, C(CH$_3$)$_3$), 0.93 (s, 3H, Pd—CH$_3$). $^{13}$C{$^1$H} (75.5 MHz, CD$_2$Cl$_2$, 273 K): δ 207.1 (C=O), 137.5 (Ar—C$_p$), 133.2 (d, $^3$J$_{CP}$=4.0 Hz, Ar—C$_{ipso}$), 130.6 (Ar—C$_o$), 129.9 (Ar—C$_m$), 70.2 (—O(CH$_2$CH$_3$)$_2$), 37.6 (d, 2J$_{CP}$=23.0 Hz, —CH$_2$—), 36.4 (d, J$_{CP}$=20.0 Hz, —C(CH$_3$)$_3$), 28.8 (d, $^2$J$_{CP}$=3.8 Hz, —C(CH$_3$)$_3$), 16.2 (—O(CH$_2$CH$_3$)$_2$), −7.1 (Pd—CH$_3$). $^{31}$P{$^1$H} NMR (121 MHz, CD$_2$Cl$_2$): δ 79.3. IR (CH$_2$Cl$_2$): ν (C=O)=1613 cm$^{-1}$. Anal Calcd for C$_{53}$H$_{50}$BF$_{24}$O$_2$PPd: C, 48.11; H, 3.81. Found: C, 48.19; H, 3.74.

EXAMPLE 221

Synthesis of 33: 31 (0.200 g, 0.48 mmol) and NaBAr'$_4$ (0.442 g, 0.50 mL) were added to a Schlenk flask and cooled to −78° C. Methylene chloride (20 mL) and 0.50 mL acetonitrile (9.49 mmol, 20 eq.) were added via syringe. The resulting pale-yellow solution was allowed to slowly warm to RT and stirred for 3 h. The yellow solution was isolated from the gray solid NaCl precipitate via cannula filtration, and the solvent was removed in vacuo to yield a yellow-brown oily residue. Pentane (20 mL) was added and the mixture was vigorously stirred for 2 h, during which time a white-gray solid precipitated from the clear, colorless solution. The product was isolated by filtration, washed with pentane (2×15 mL), and dried in vacuo to yield 33 (0.478 g, 78% yield). The product was recrystallized from diethyl ether/pentane. $^1$H NMR (400 MHz, CD$_2$Cl$_2$): δ 8.05 (d, 2H, J=8.6 Hz, Ar—H$_o$), 7.80 (t, 1H, J=7.6 Hz, Ar—H$_p$), 7.58 (m, 2H, Ar—H$_m$), 3.65 (d, 2H, $^2$J$_{HP}$=9.2 Hz, —CH$_2$—), 2.35 (s, 3H, —NCCH$_3$), 1.37 (d, 18H, $^3$J$_{HP}$=15.2 Hz, —C(CH$_3$)$_3$), 0.97 (s, 3H, Pd—CH$_3$). $^{13}$C{$^1$H} NMR (75.5 MHz, CD$_2$Cl$_2$, 273 K): δ 207.4 (C=O), 137.2 (Ar—C$_p$), 133.4 (d, $^3$J$_{CP}$=4.2 Hz, Ar—C$_{ipso}$), 130.6 (Ar—C$_0$), 129.8 (Ar—C$_m$), 118.5 (—NCCH$_3$), 37.1 d, J$_{CP}$=22.6 Hz, —CH$_2$—), 35.9 (d, J$_{CP}$=19.6 Hz, —C(CH$_3$)$_3$), 28.8 (d, $^2$J$_{CP}$=4 Hz, —C(CH$_3$)$_3$), 3.2 (—NCCH$_3$), −10.4 (Pd—CH$_3$). $^{31}$P{$^1$H) NMR (162 MHz, CD$_2$Cl$_2$): δ 75.2. IR (CH$_2$Cl$_2$): ν (C=O)=1617 cm$^{-1}$. Anal Calcd for C$_{51}$H$_{43}$BF$_{24}$NOPPd: C, 47.50; H, 3.36; N, 1.09. Found: C, 47.73; H, 3.33; N, 1.22.

EXAMPLES 222–233

General Procedure for 0 MPa Polymerizations: 32 or 33 (10.0 μmol) was added to a flame-dried Schlenk flask under argon. The flask was backfilled three times with 1 atm ethylene (0 Pa, gauge) and charged with 25 mL toluene. The flask was immediately placed into an oil bath (warmed to the desired reaction temperature) and stirred under 0 Pa ethylene for the 3 h. The reaction was quenched with acetone and the volatiles were removed in vacuo. The residue was extracted into hexanes and passed through a plug of 2:1 silica gel/alumina. The solvent was removed on a rotovap and the resulting clear, colorless oil was dried in vacuo.

General Procedure for 1.38 MPa Polymerizations: A 1000 mL Parr® autoclave was heated under vacuum at 100° C. for 1 h and was then cooled and backfilled with ethylene. Toluene (200 mL) was added, the autoclave was sealed, and the ethylene pressure was raised to ca. 3 atm. The reactor temperature was established and the solvent was allowed to stir for 10 min. The autoclave was then vented, the catalyst solution (3.88 μmol 32 or 33 in 5 mL toluene) was added, and the autoclave was sealed and pressurized to 1.38 MPa ethylene pressure while stirring for 3 h. The reaction was quenched by venting the autoclave followed by addition of acetone. The contents were transferred to a 500 mL RB flask and the solvent was removed on a rotovap. The residue was extracted into hot toluene and filtered to removed Pd black. The solvent was removed and the resulting colorless amorphous solid was dried in vacuo.

Results all polymerizations are given in Table 38.

TABLE 38

| Ex. | Pres. MPa | cat. | temp. (° C.) | yield (g) | TON[a] | M$_w$[b] |
|---|---|---|---|---|---|---|
| 222 | 0 | 32 | 25 | 0.204 | 720 | 300[f] |
| 223 | 0 | 32 | 60 | 0.612 | 2200 | 300 |
| 224 | 0 | 33 | 25 | 0.009 | 30 | 350 |
| 225 | 0 | 33 | 60 | 0.352 | 1300 | 330 |
| 226 | 1.38 | 32 | 25 | 0.135 | 1200 | 380 |
| 226 | 1.38 | 32 | 40 | 0.497 | 4600 | 280 |
| 228 | 1.38 | 32 | 60 | 1.971 | 18100 | 290 |
| 229 | 1.38 | 32 | 80 | 6.582 | 60500 | 280 |
| 230 | 1.38 | 33 | 25 | 0.052 | 500 | 400 |
| 231 | 1.38 | 33 | 40 | 0.427 | 3900 | 370 |
| 232 | 1.38 | 33 | 60 | 2.445 | 22500 | 370 |
| 233 | 1.38 | 33 | 80 | 6.526 | 60000 | 340 |

[a]TON mol PE per mol catalyst.
[b]Determined by GPC.

EXAMPLE 234

The following illustrates a test for an "active ligand". A series of ethylene homopolymerizations and copolymerizations were carried out under the conditions of Test 1 or Test 2 for "active ligands," or under conditions close to those described. The catalyst was F-5, and the polymerizatsions were carried out at 5.52 MPa ethylene pressure and 100° C. The results are presented in Table 39. From the results in Table 39, F5 qualifies as an active ligand under both of Tests 1 and 2 for active catalysts.

TABLE 39

| Polymer Yield (g) | mmol cat. | Co-catalyst and additives | Time (h) |
|---|---|---|---|
| 16.95 | 0.0085 | 10 eq. B(Ph)$_3$ | 1 |
| 15.97 | 0.0085 | 10 eq B(C$_6$F$_5$)$_3$ | 1 |
| 14.26 | 0.0085 | none | 1 |
| 5.13 | 0.0092 | No borane 60 mL E-10-U | 2 |

TABLE 39-continued

| Polymer Yield (g) | mmol cat. | Co-catalyst and additives | Time (h) |
|---|---|---|---|
| 4.61 | 0.0092 | 10 eq B(C$_6$F$_5$)$_3$ 60 mL E-10-U | 2 |

What is claimed is:

1. A process for the polymerization of olefins, comprising the step of contacting, under polymerizing conditions, one or more polymerizable olefins with an active polymerization catalyst comprising a group 3 through 11 (IUPAC) transition metal or lanthanide metal complex of a ligand of the formula (I)

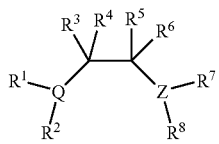

wherein:

Z is nitrogen and Q is phosphorus, or Z is oxygen and Q is phosphorus, or Z is oxygen and Q is nitrogen;

provided that:

when Q is phosphorous and Z is nitrogen:
- $R^1$ and $R^2$ are each independently hydrocarbyl, silyl, or substituted hydrocarbyl having an $E_s$ of about −0.90 or less;
- $R^3$, $R^4$, $R^5$, and $R^6$ are each independently hydrogen, hydrocarbyl, a functional group, or substituted hydrocarbyl;
- $R^7$ is hydrogen, hydrocarbyl, substituted hydrocarbyl or silyl; and
- $R^8$ is hydrocarbyl, substituted hydrocarbyl, or silyl;
- provided that any two of $R^3$, $R^4$, $R^5$, $R^6$, $R^7$ and $R^8$ vicinal or geminal to one another together may form a ring;

when Q is phosphorous and Z is oxygen:
- $R^1$ and $R^2$ are each independently hydrocarbyl, silyl, or substituted hydrocarbyl having an $E_s$ of about −0.90 or less;
- $R^3$ and $R^4$ are each independently hydrogen, hydrocarbyl, a functional group, or substituted hydrocarbyl;
- $R^5$ and $R^7$ taken together form a double bond;
- $R^8$ is not present; and
- $R^6$ is —OR$^9$, —NR$^{10}$R$^{11}$, hydrocarbyl or substituted hydrocarbyl,
  - wherein $R^9$ is hydrocarbyl or substituted hydrocarbyl, and
  - $R^{10}$ and $R^{11}$ are each independently hydrogen, hydrocarbyl or substituted hydrocarbyl; and
- provided that any two of $R^3$, $R^4$, and $R^6$ vicinal or geminal to one another may form a ring; or
- $R^1$ and $R^2$ are each independently hydrocarbyl, silyl, or substituted hydrocarbyl having an $E_s$ of about −0.90 or less;
- $R^3$, $R^4$, $R^5$ and $R^6$ are each independently hydrogen, hydrocarbyl, a functional group, or substituted hydrocarbyl;
- $R^7$ is hydrocarbyl, silyl, or substituted hydrocarbyl; and
- $R^8$ is not present; and
- provided that any two of $R^3$, $R^4$, $R^5$, $R^6$, and $R^7$ vicinal or geminal to one another may form a ring;

when Q is nitrogen:
- $R^1$ is hydrocarbyl, silyl, or substituted hydrocarbyl having an $E_s$ of about −0.90 or less;
- $R^2$ and $R^3$ are each independently hydrogen, hydrocarbyl, a functional group, or substituted hydrocarbyl, or taken together form a double bond;
- $R^4$ is hydrogen, hydrocarbyl, a functional group, or substituted hydrocarbyl; Z is oxygen;
- $R^6$ and $R^7$ taken together form a double bond;
- $R^8$ is not present;
- $R^5$ is —OR$^{12}$, —R$^{13}$ or —NR$^{14}$R$^{15}$, wherein $R^{12}$ and $R^{13}$ are each independently hydrocarbyl or substituted hydrocarbyl, and
- $R^{14}$ and $R^{15}$ are each hydrogen, hydrocarbyl or substituted hydrocarbyl;
- provided that when $R^2$ and $R^3$ taken together form an aromatic ring, $R^1$ and $R^4$ are not present; and
- further provided that any two of $R^2$, $R^3$, $R^4$ and $R^5$ vicinal or germinal to one another taken together may form a ring.

2. The process of claim 1, wherein said one or more polymerizable olefins are compounds of the formula H$_2$C=CH(CH$_2$)$_n$G (VIII), wherein n is 0 or an integer of 1 or more, G is hydrogen or —CO$_2$R$^{25}$, and R$^{25}$ is hydrogen, hydrocarbyl or substituted hydrocarbyl.

3. The process of claim 2, wherein said one or more polymerizable olefins comprises ethylene.

4. The process of claim 3, wherein said one or more polymerizable olefins comprises ethylene and at least one other polymerizable olefin.

* * * * *